US012599337B1

(12) United States Patent
Windmiller et al.

(10) Patent No.: US 12,599,337 B1
(45) Date of Patent: Apr. 14, 2026

(54) METHOD AND SYSTEM FOR CONFIRMATION OF MICRONEEDLE-BASED ANALYTE-SELECTIVE SENSOR INSERTION INTO VIABLE TISSUE VIA ELECTRICAL INTERROGATION

(71) Applicant: Biolinq Incorporated, San Diego, CA (US)

(72) Inventors: Joshua Windmiller, San Diego, CA (US); Jared Rylan Tangney, Encinitas, CA (US)

(73) Assignee: Biolinq Incorporated, San Diego, CA (US)

( * ) Notice: Subject to any disclaimer, the term of this patent is extended or adjusted under 35 U.S.C. 154(b) by 71 days.

(21) Appl. No.: 16/051,398

(22) Filed: Jul. 31, 2018

Related U.S. Application Data

(60) Provisional application No. 62/542,774, filed on Aug. 8, 2017.

(51) Int. Cl.
*A61B 5/00* (2006.01)
*A61B 5/0531* (2021.01)
(Continued)

(52) U.S. Cl.
CPC .......... *A61B 5/685* (2013.01); *A61B 5/14532* (2013.01); *A61B 5/14546* (2013.01);
(Continued)

(58) Field of Classification Search
CPC ............ A61B 5/14532; A61B 5/14546; A61B 5/14865; A61B 5/685; C12Q 1/006; G01N 33/48785
See application file for complete search history.

(56) References Cited

U.S. PATENT DOCUMENTS 3,964,482 A 6/1976 Gerstel et al.
4,305,401 A 12/1981 Reissmueller et al.
(Continued)

FOREIGN PATENT DOCUMENTS

CN 101068591 A 11/2007
CN 108845012 A 11/2018
(Continued)

OTHER PUBLICATIONS

Fabrication of a Microneedle/CNT Hierarchical Micro/Nano Surface Electrochemical Sensor and Its In-Vitro Glucose Sensing Characterization; Youngsam Yoon, Gil S. Lee, Koangki Yoo, Jeong-Bong Lee; Sensors 2013, 13, 16672-16681; doi: 10.3390/s131216672 (Year: 2013).*
(Continued)

*Primary Examiner* — Jennifer Robertson
*Assistant Examiner* — Karen E Toth
(74) *Attorney, Agent, or Firm* — Cooley LLP

(57) ABSTRACT

A system and method to confirm the insertion of an analyte-selective sensor comprising an array of microneedles possessing vertical extent between 200 and 2000 µm into viable tissue is disclosed herein. Mechanical insertion of an analyte-selective sensor is firstly attempted by means of an application of external force. Either during or following this routine, an electrical stimulus is applied between at least two distinct electrodes located within the said analyte-selective sensor; a resultant response is measured. This response is compared with a reference value to determine if insertion was successful. If insertion was successful, no further effort is required and the sensor can operate as intended. However, if insertion was not successful, the user can be instructed to continue to apply additional force to said sensor to achieve successful insertion or otherwise re-apply the said sensor altogether.

18 Claims, 7 Drawing Sheets

(51) Int. Cl.
    *A61B 5/145*         (2006.01)
    *C12Q 1/00*          (2006.01)
    *G01N 27/327*       (2006.01)
    *G16H 40/40*        (2018.01)

(52) U.S. Cl.
    CPC ........... *C12Q 1/001* (2013.01); *G01N 27/327*
        (2013.01); *G01N 27/3271* (2013.01); *G16H*
           *40/40* (2018.01); *A61B 5/0531* (2013.01);
                      *A61B 2562/0295* (2013.01)

(56) References Cited

U.S. PATENT DOCUMENTS

| | | | |
|---|---|---|---|
| 4,323,996 A | 4/1982 | Ganter | |
| 4,407,295 A | 10/1983 | Steuer et al. | |
| 4,450,842 A | 5/1984 | Zick et al. | |
| 4,908,117 A | 3/1990 | Kinlen et al. | |
| 4,969,468 A | 11/1990 | Byers et al. | |
| 5,035,711 A | 7/1991 | Aoki et al. | |
| 5,131,390 A | 7/1992 | Sakaguchi et al. | |
| 5,215,088 A | 6/1993 | Normann et al. | |
| 5,279,543 A | 1/1994 | Glikfeld et al. | |
| 5,286,364 A | 2/1994 | Yacynych et al. | |
| 5,540,828 A | 7/1996 | Yacynych | |
| 5,730,714 A | 3/1998 | Guy et al. | |
| 5,766,132 A | 6/1998 | Yasukawa et al. | |
| 5,832,410 A | 11/1998 | Lin et al. | |
| 5,869,078 A | 2/1999 | Baudino | |
| 5,953,306 A | 9/1999 | Yi | |
| 6,036,055 A | 3/2000 | Mogadam et al. | |
| 6,091,975 A | 7/2000 | Daddona et al. | |
| 6,104,940 A | 8/2000 | Watanabe et al. | |
| 6,132,449 A | 10/2000 | Lum et al. | |
| 6,132,499 A | 10/2000 | Wong et al. | |
| 6,132,755 A | 10/2000 | Eicher et al. | |
| 6,139,718 A | 10/2000 | Kurnik et al. | |
| 6,175,752 B1 | 1/2001 | Say et al. | |
| 6,269,053 B1 | 7/2001 | Kawata et al. | |
| 6,284,126 B1 | 9/2001 | Kurnik et al. | |
| 6,364,890 B1 | 4/2002 | Lum et al. | |
| 6,413,396 B1 | 7/2002 | Yang et al. | |
| 6,465,091 B1 | 10/2002 | Ou-Yang | |
| 6,471,903 B2 | 10/2002 | Sherman et al. | |
| 6,527,762 B1 | 3/2003 | Santini, Jr. et al. | |
| 6,551,849 B1 | 4/2003 | Kenney | |
| 6,587,705 B1 | 7/2003 | Kim et al. | |
| 6,599,408 B1 | 7/2003 | Chan et al. | |
| 6,603,987 B2 | 8/2003 | Whitson | |
| 6,611,707 B1 | 8/2003 | Prausnitz et al. | |
| 6,793,789 B2 | 9/2004 | Choi et al. | |
| 6,801,041 B2 | 10/2004 | Karinka et al. | |
| 6,814,845 B2 | 11/2004 | Wilson et al. | |
| 6,862,466 B2 | 3/2005 | Ackerman | |
| 6,908,453 B2 | 6/2005 | Fleming et al. | |
| 7,081,195 B2 | 7/2006 | Simpson et al. | |
| 7,097,776 B2 | 8/2006 | Raju | |
| 7,132,054 B1 | 11/2006 | Kravitz et al. | |
| 7,183,068 B2 | 2/2007 | Burson et al. | |
| 7,262,068 B2 | 8/2007 | Roy et al. | |
| 7,343,188 B2 | 3/2008 | Sohrab | |
| 7,344,499 B1 | 3/2008 | Prausnitz et al. | |
| 7,366,556 B2 | 4/2008 | Brister et al. | |
| 7,415,299 B2 | 8/2008 | Zimmermann et al. | |
| 7,429,333 B2 | 9/2008 | Chiou et al. | |
| 7,456,112 B2 | 11/2008 | Lee | |
| 7,471,972 B2 | 12/2008 | Rhodes et al. | |
| 7,473,244 B2 | 1/2009 | Frazier et al. | |
| 7,493,232 B1 | 2/2009 | Surina | |
| 7,534,330 B2 | 5/2009 | Yu et al. | |
| 7,583,990 B2 | 9/2009 | Goode, Jr. | |
| 7,599,726 B2 | 10/2009 | Goode, Jr. | |
| 7,613,491 B2 | 11/2009 | Boock | |
| 7,645,263 B2 | 1/2010 | Angel et al. | |
| 7,715,893 B2 | 5/2010 | Kamath et al. | |
| 7,725,148 B2 | 5/2010 | Shah et al. | |
| 7,768,408 B2 | 8/2010 | Reggiardo et al. | |
| 7,778,680 B2 | 8/2010 | Goode, Jr. | |
| 7,797,028 B2 | 9/2010 | Goode, Jr. | |
| 7,811,231 B2 | 10/2010 | Jin et al. | |
| 7,837,654 B2 | 11/2010 | Shumate et al. | |
| 7,885,697 B2 | 2/2011 | Brister et al. | |
| 7,905,833 B2 | 3/2011 | Brister et al. | |
| 7,917,186 B2 | 3/2011 | Kamath et al. | |
| 7,949,382 B2 | 5/2011 | Jina | |
| 7,959,569 B2 | 6/2011 | Goode et al. | |
| 8,005,526 B2 | 8/2011 | Martin et al. | |
| 8,010,174 B2 | 8/2011 | Goode, Jr. | |
| 8,022,292 B2 | 9/2011 | Arianpour et al. | |
| 8,064,977 B2 | 11/2011 | Boock et al. | |
| 8,088,321 B2 | 1/2012 | Ferguson et al. | |
| 8,094,009 B2 | 1/2012 | Allen et al. | |
| 8,108,023 B2 | 1/2012 | Mir et al. | |
| 8,110,079 B2 | 2/2012 | Gooding et al. | |
| 8,125,331 B2 | 2/2012 | Allen et al. | |
| 8,130,095 B2 | 3/2012 | Allen et al. | |
| 8,160,665 B2 | 4/2012 | Mischler et al. | |
| 8,160,671 B2 | 4/2012 | Kamath et al. | |
| 8,160,834 B2 | 4/2012 | Liang et al. | |
| 8,162,901 B2 | 4/2012 | Gonnelli et al. | |
| RE43,399 E | 5/2012 | Simpson et al. | |
| 8,216,138 B1 | 7/2012 | McGarraugh | |
| 8,236,368 B2 | 8/2012 | Jung et al. | |
| 8,249,684 B2 | 8/2012 | Kamath et al. | |
| 8,257,324 B2 | 9/2012 | Prausnitz et al. | |
| 8,280,475 B2 | 10/2012 | Brister et al. | |
| 8,280,476 B2 | 10/2012 | Jina | |
| 8,284,046 B2 | 10/2012 | Allen et al. | |
| 8,287,453 B2 | 10/2012 | Li et al. | |
| 8,308,960 B2 | 11/2012 | Kalvesten et al. | |
| 8,346,335 B2 | 1/2013 | Harper et al. | |
| 8,376,945 B2 | 2/2013 | Hayter et al. | |
| 8,386,004 B2 | 2/2013 | Kamath et al. | |
| 8,423,114 B2 | 4/2013 | Simpson et al. | |
| 8,428,678 B2 | 4/2013 | Kamath et al. | |
| 8,452,369 B2 | 5/2013 | Huys et al. | |
| 8,463,350 B2 | 6/2013 | Kamath et al. | |
| 8,483,793 B2 | 7/2013 | Simpson et al. | |
| 8,506,529 B1 | 8/2013 | Yang | |
| 8,548,553 B2 | 10/2013 | Kamath et al. | |
| 8,565,848 B2 | 10/2013 | Brister et al. | |
| 8,574,165 B2 | 11/2013 | Marsh | |
| 8,617,069 B2 | 12/2013 | Bernstein et al. | |
| RE44,695 E | 1/2014 | Simpson et al. | |
| 8,626,257 B2 | 1/2014 | Li et al. | |
| 8,637,351 B2 | 1/2014 | Kalvesten et al. | |
| 8,660,628 B2 | 2/2014 | Wang et al. | |
| 8,700,114 B2 | 4/2014 | Gottlieb et al. | |
| 8,708,966 B2 | 4/2014 | Allen et al. | |
| 8,798,799 B2 | 8/2014 | Deo et al. | |
| 8,815,070 B2 | 8/2014 | Wang et al. | |
| 8,870,763 B2 | 10/2014 | Yang et al. | |
| 8,882,665 B2 | 11/2014 | Yang et al. | |
| 9,008,743 B2 | 4/2015 | Hayter et al. | |
| 9,008,745 B2 | 4/2015 | Pushpala et al. | |
| 9,055,901 B2 | 6/2015 | Brister et al. | |
| 9,125,625 B2 | 9/2015 | Wang et al. | |
| 9,182,368 B2 | 11/2015 | Pushpala et al. | |
| 9,234,872 B2 | 1/2016 | Homyk et al. | |
| 9,248,273 B2 | 2/2016 | Guvanasen et al. | |
| 9,332,934 B2 | 5/2016 | Hayter et al. | |
| 9,336,423 B2 | 5/2016 | Goodnow et al. | |
| 9,357,951 B2 | 6/2016 | Simpson et al. | |
| 9,386,954 B2 | 7/2016 | Saini et al. | |
| 9,387,000 B2 | 7/2016 | Corrie et al. | |
| 9,414,778 B2 | 8/2016 | Mao et al. | |
| 9,420,965 B2 | 8/2016 | Brauker et al. | |
| 9,498,155 B2 * | 11/2016 | Brauker ............. A61B 5/14532 |
| 9,532,741 B2 | 1/2017 | Brauker et al. | |
| 9,551,698 B2 | 1/2017 | Huys et al. | |
| 9,662,056 B2 | 5/2017 | Budiman et al. | |
| 9,737,247 B2 | 8/2017 | Wang et al. | |
| 9,743,870 B2 | 8/2017 | Wang et al. | |
| 9,743,871 B2 | 8/2017 | Simpson et al. | |
| 9,757,061 B2 | 9/2017 | Shults et al. | |

(56)                 References Cited

U.S. PATENT DOCUMENTS

| | | |
|---|---|---|
| 9,770,211 B2 | 9/2017 | Hayter et al. |
| 9,804,114 B2 | 10/2017 | Rhodes et al. |
| 9,933,387 B1 | 4/2018 | McCanna et al. |
| 9,958,409 B2 | 5/2018 | Gerber et al. |
| 10,022,076 B2 | 7/2018 | Hoss et al. |
| 10,039,480 B2 | 8/2018 | Brauker et al. |
| 10,046,114 B1 | 8/2018 | Biederman et al. |
| 10,052,055 B2 | 8/2018 | Li et al. |
| 10,092,207 B1 | 10/2018 | Windmiller |
| 10,136,846 B2 | 11/2018 | Wang et al. |
| 10,173,042 B2 | 1/2019 | Pushpala et al. |
| 10,182,748 B2 | 1/2019 | Catt et al. |
| 10,188,333 B2 | 1/2019 | Kamath et al. |
| 10,228,341 B2 | 3/2019 | Katsuki et al. |
| 10,299,712 B2 | 5/2019 | Brister et al. |
| 10,327,678 B2 | 6/2019 | Gottlieb et al. |
| 10,492,708 B1 | 12/2019 | Windmiller |
| D875,254 S | 2/2020 | Cooke et al. |
| 10,549,080 B2 | 2/2020 | Pushpala et al. |
| 10,610,103 B2 | 4/2020 | Brister et al. |
| 10,709,332 B2 | 7/2020 | Brister et al. |
| 10,743,800 B2 | 8/2020 | Larvenz et al. |
| 10,780,222 B2 | 9/2020 | Ward et al. |
| 10,820,860 B2 | 11/2020 | Pushpala et al. |
| 10,881,334 B2 | 1/2021 | Facchinetti et al. |
| 10,932,700 B2 | 3/2021 | Simpson et al. |
| 10,983,083 B2 | 4/2021 | Harding et al. |
| 11,020,026 B2 | 6/2021 | Boock et al. |
| 11,035,872 B2 | 6/2021 | Boutelle et al. |
| 11,045,142 B1 | 6/2021 | Windmiller et al. |
| 11,051,724 B2 | 7/2021 | Pace et al. |
| 11,123,532 B2 | 9/2021 | Pushpala et al. |
| 11,179,068 B2 | 11/2021 | Pace et al. |
| 11,197,985 B2 | 12/2021 | Pushpala et al. |
| 11,272,866 B2 | 3/2022 | Pushpala et al. |
| 11,272,885 B2 | 3/2022 | Pushpala et al. |
| 11,291,390 B2 | 4/2022 | Pushpala et al. |
| 11,331,022 B2 | 5/2022 | Halac et al. |
| 11,359,300 B1 | 6/2022 | Beer et al. |
| 11,406,818 B2 | 8/2022 | Windmiller |
| 11,478,194 B2 | 10/2022 | Windmiller et al. |
| 11,596,332 B2 | 3/2023 | Shults et al. |
| 11,654,270 B2 | 5/2023 | Mansfield et al. |
| D988,160 S | 6/2023 | Morelock |
| 11,672,965 B2 | 6/2023 | Mansfield et al. |
| 11,697,007 B2 | 7/2023 | Gu et al. |
| D996,999 S | 8/2023 | Morelock |
| 11,819,650 B2 | 11/2023 | Pushpala et al. |
| D1,012,744 S | 1/2024 | Morelock |
| 11,857,344 B2 | 1/2024 | Windmiller et al. |
| 11,865,289 B2 | 1/2024 | Pushpala et al. |
| 11,872,055 B2 | 1/2024 | Tangney et al. |
| D1,013,544 S | 2/2024 | Morelock |
| 11,896,792 B2 | 2/2024 | Pushpala et al. |
| 11,896,793 B2 | 2/2024 | Pushpala et al. |
| 11,903,738 B2 | 2/2024 | Pushpala et al. |
| 11,904,127 B2 | 2/2024 | Mansfield et al. |
| 11,963,796 B1 | 4/2024 | Windmiller |
| 11,986,614 B2 | 5/2024 | Mansfield et al. |
| 11,992,314 B2 | 5/2024 | Hahn et al. |
| 12,011,294 B2 | 6/2024 | Campbell et al. |
| D1,033,641 S | 7/2024 | Morelock |
| D1,035,004 S | 7/2024 | Morelock |
| 12,048,558 B2 | 7/2024 | Kendall et al. |
| D1,038,794 S | 8/2024 | Morelock |
| 12,070,307 B2 | 8/2024 | Ebejer et al. |
| 12,070,313 B2 | 8/2024 | Fuchs et al. |
| 12,109,032 B1 | 10/2024 | Windmiller et al. |
| D1,051,745 S | 11/2024 | Morelock |
| D1,057,153 S | 1/2025 | Morelock |
| D1,068,516 S | 4/2025 | Morelock |
| 12,279,888 B2 | 4/2025 | Campbell et al. |
| 12,285,271 B2 | 4/2025 | Campbell et al. |
| 12,336,816 B2 | 6/2025 | Campbell et al. |
| D1,083,640 S | 7/2025 | Morelock |
| D1,083,977 S | 7/2025 | Morelock |
| 12,369,830 B2 | 7/2025 | Windmiller et al. |
| 2002/0004640 A1 | 1/2002 | Conn et al. |
| 2002/0020688 A1 | 2/2002 | Sherman et al. |
| 2002/0055704 A1 | 5/2002 | Scott et al. |
| 2002/0072784 A1 | 6/2002 | Norman, Jr. et al. |
| 2002/0105080 A1 | 8/2002 | Speakman |
| 2002/0120186 A1 | 8/2002 | Keimel |
| 2002/0187556 A1 | 12/2002 | Shartle et al. |
| 2003/0068666 A1 | 4/2003 | Zweig |
| 2003/0088166 A1 | 5/2003 | Say et al. |
| 2003/0095582 A1 | 5/2003 | Ackley |
| 2003/0100040 A1 | 5/2003 | Bonnecaze et al. |
| 2003/0104119 A1 | 6/2003 | Wilson et al. |
| 2003/0135158 A1 | 7/2003 | Gonnelli |
| 2003/0199788 A1 | 10/2003 | Erickson et al. |
| 2003/0208167 A1 | 11/2003 | Prausnitz et al. |
| 2003/0225360 A1 | 12/2003 | Eppstein et al. |
| 2003/0235817 A1 | 12/2003 | Bartkowiak et al. |
| 2004/0065158 A1 | 4/2004 | Schrepfer et al. |
| 2004/0082875 A1 | 4/2004 | Donoghue et al. |
| 2004/0138543 A1 | 7/2004 | Russell et al. |
| 2004/0189311 A1 | 9/2004 | Glezer et al. |
| 2004/0220625 A1* | 11/2004 | Silvestri .................. A61N 1/37 |
| | | 607/4 |
| 2005/0036020 A1 | 2/2005 | Li et al. |
| 2005/0101841 A9 | 5/2005 | Kaylor et al. |
| 2005/0137536 A1 | 6/2005 | Gonnelli |
| 2005/0209565 A1 | 9/2005 | Yuzhakov et al. |
| 2005/0267440 A1 | 12/2005 | Herman et al. |
| 2005/0272989 A1 | 12/2005 | Shah et al. |
| 2006/0015061 A1 | 1/2006 | Kuo et al. |
| 2006/0016700 A1* | 1/2006 | Brister ................. A61B 5/6848 |
| | | 205/777.5 |
| 2006/0173259 A1 | 8/2006 | Flaherty et al. |
| 2006/0264716 A1 | 11/2006 | Zander |
| 2006/0281121 A1 | 12/2006 | Unger et al. |
| 2007/0060815 A1 | 3/2007 | Martin et al. |
| 2007/0078445 A1 | 4/2007 | Malloy |
| 2007/0169533 A1* | 7/2007 | Shah .................... G01N 27/327 |
| | | 73/1.01 |
| 2007/0170054 A2 | 7/2007 | Wilsey |
| 2007/0191733 A1 | 8/2007 | Gianchandani et al. |
| 2007/0213044 A1 | 9/2007 | Steingart et al. |
| 2007/0282246 A1 | 12/2007 | Henley |
| 2008/0009800 A1 | 1/2008 | Nickel |
| 2008/0009801 A1 | 1/2008 | Nickel |
| 2008/0027369 A1 | 1/2008 | Carter et al. |
| 2008/0027426 A1 | 1/2008 | Kelly et al. |
| 2008/0033269 A1 | 2/2008 | Zhang |
| 2008/0097280 A1 | 4/2008 | Martin et al. |
| 2008/0097352 A1 | 4/2008 | Beck et al. |
| 2008/0119707 A1 | 5/2008 | Stafford |
| 2008/0154107 A1 | 6/2008 | Jina |
| 2008/0156661 A1* | 7/2008 | Cooper ................. A61B 5/6848 |
| | | 205/775 |
| 2008/0213461 A1 | 9/2008 | Gill et al. |
| 2008/0221408 A1 | 9/2008 | Hoarau et al. |
| 2008/0234562 A1 | 9/2008 | Jina |
| 2008/0255434 A1* | 10/2008 | Hayter ................. A61B 5/1473 |
| | | 600/309 |
| 2008/0275327 A1 | 11/2008 | Faarbaek et al. |
| 2008/0319298 A1 | 12/2008 | Huys et al. |
| 2009/0043250 A1 | 2/2009 | Gonnelli |
| 2009/0057148 A1 | 3/2009 | Wieder et al. |
| 2009/0062752 A1 | 3/2009 | Gonnelli |
| 2009/0066348 A1 | 3/2009 | Shin et al. |
| 2009/0069651 A1 | 3/2009 | Zimmermann et al. |
| 2009/0069697 A1 | 3/2009 | Frazier et al. |
| 2009/0084678 A1 | 4/2009 | Joshi et al. |
| 2009/0088652 A1 | 4/2009 | Tremblay |
| 2009/0090623 A1 | 4/2009 | Chuang et al. |
| 2009/0099427 A1 | 4/2009 | Jina et al. |
| 2009/0101498 A1 | 4/2009 | Papadimitrakopoulos et al. |
| 2009/0118672 A1 | 5/2009 | Gonnelli et al. |
| 2009/0131778 A1 | 5/2009 | Jina et al. |
| 2009/0143761 A1 | 6/2009 | Cantor et al. |
| 2009/0152598 A1 | 6/2009 | Baek et al. |
| 2009/0191616 A1 | 7/2009 | Lu et al. |

(56) References Cited

U.S. PATENT DOCUMENTS

| 2009/0198118 A1 | 8/2009 | Hayter et al. |
| 2009/0218239 A1 | 9/2009 | Gooding et al. |
| 2009/0259118 A1 | 10/2009 | Feldman et al. |
| 2009/0294306 A1 | 12/2009 | Feldman et al. |
| 2009/0301994 A1 | 12/2009 | Bhandari et al. |
| 2010/0006451 A1 | 1/2010 | Gordon et al. |
| 2010/0021637 A1 | 1/2010 | Revol et al. |
| 2010/0022416 A1 | 1/2010 | Flemming et al. |
| 2010/0025238 A1 | 2/2010 | Gottlieb et al. |
| 2010/0030045 A1 | 2/2010 | Gottlieb et al. |
| 2010/0049021 A1 | 2/2010 | Jina et al. |
| 2010/0052892 A1 | 3/2010 | Allen et al. |
| 2010/0052897 A1 | 3/2010 | Allen et al. |
| 2010/0052898 A1 | 3/2010 | Allen et al. |
| 2010/0052915 A1 | 3/2010 | Allen et al. |
| 2010/0056873 A1 | 3/2010 | Allen et al. |
| 2010/0108509 A1 | 5/2010 | Curry et al. |
| 2010/0137779 A1 | 6/2010 | Seitz |
| 2010/0160756 A1 | 6/2010 | Petisce et al. |
| 2010/0200538 A1 | 8/2010 | Petisce et al. |
| 2010/0279377 A1 | 11/2010 | Shah et al. |
| 2010/0286803 A1 | 11/2010 | Tillotson |
| 2011/0027127 A1 | 2/2011 | Simpson et al. |
| 2011/0042241 A1 | 2/2011 | Kotsis et al. |
| 2011/0077490 A1 | 3/2011 | Simpson et al. |
| 2011/0105871 A1 | 5/2011 | Zimmermann et al. |
| 2011/0140703 A1 | 6/2011 | Chiao et al. |
| 2011/0196216 A1 | 8/2011 | Quarder et al. |
| 2011/0210017 A1 | 9/2011 | Lai et al. |
| 2011/0224515 A1 | 9/2011 | Mir et al. |
| 2011/0230736 A1 | 9/2011 | Tepper et al. |
| 2011/0237925 A1 | 9/2011 | Yue et al. |
| 2011/0247934 A1 | 10/2011 | Wang et al. |
| 2011/0275918 A1 | 11/2011 | Yamashita et al. |
| 2011/0306853 A1 | 12/2011 | Black et al. |
| 2011/0319787 A1 | 12/2011 | Lamoise et al. |
| 2012/0018302 A1 | 1/2012 | Shiraki et al. |
| 2012/0037515 A1 | 2/2012 | Solanki |
| 2012/0067734 A1 | 3/2012 | Wang et al. |
| 2012/0078071 A1* | 3/2012 | Bohm ............... A61B 5/14532 |
| | | 600/345 |
| 2012/0123232 A1 | 5/2012 | Najarian et al. |
| 2012/0172692 A1 | 7/2012 | Tamada et al. |
| 2012/0209244 A1 | 8/2012 | Gray |
| 2012/0277629 A1 | 11/2012 | Bernstein et al. |
| 2012/0323097 A9 | 12/2012 | Chowdhury |
| 2013/0053660 A1 | 2/2013 | Shieh |
| 2013/0065257 A1 | 3/2013 | Wang et al. |
| 2013/0135158 A1 | 5/2013 | Faraone et al. |
| 2013/0144131 A1 | 6/2013 | Wang et al. |
| 2013/0158376 A1 | 6/2013 | Hayter et al. |
| 2013/0225956 A1 | 8/2013 | Huang et al. |
| 2013/0281808 A1 | 10/2013 | Shieh |
| 2013/0324820 A1 | 12/2013 | Petillo et al. |
| 2013/0338632 A1 | 12/2013 | Kaplan et al. |
| 2013/0338746 A1 | 12/2013 | Guvanasen et al. |
| 2013/0345597 A1 | 12/2013 | Hagino et al. |
| 2014/0135679 A1 | 5/2014 | Mann et al. |
| 2014/0259652 A1 | 9/2014 | Pushpala et al. |
| 2014/0275897 A1 | 9/2014 | Pushpala et al. |
| 2014/0275899 A1 | 9/2014 | Gottlieb et al. |
| 2014/0275907 A1 | 9/2014 | Feldman et al. |
| 2014/0303471 A1 | 10/2014 | Rajaraman et al. |
| 2014/0336487 A1* | 11/2014 | Wang ............... A61B 5/150984 |
| | | 600/352 |
| 2014/0378804 A1 | 12/2014 | Kalvesten et al. |
| 2015/0073238 A1* | 3/2015 | Matsumoto ........ A61B 5/14503 |
| | | 600/302 |
| 2015/0126834 A1 | 5/2015 | Wang et al. |
| 2015/0186609 A1 | 7/2015 | Utter, II |
| 2015/0208970 A1 | 7/2015 | Huang |
| 2015/0243851 A1 | 8/2015 | Lee et al. |
| 2015/0250421 A1 | 9/2015 | Arumugam et al. |
| 2015/0276758 A1 | 10/2015 | Addisu |
| 2015/0313527 A1 | 11/2015 | Renlund |
| 2016/0022187 A1 | 1/2016 | Pushpala et al. |
| 2016/0029937 A1 | 2/2016 | Sia et al. |
| 2016/0058342 A1 | 3/2016 | Maiz-Aquinaga et al. |
| 2016/0095541 A1 | 4/2016 | Wang et al. |
| 2016/0095547 A1 | 4/2016 | Wang et al. |
| 2016/0139069 A1 | 5/2016 | Wang |
| 2016/0157764 A1 | 6/2016 | Di Palma et al. |
| 2016/0158514 A1 | 6/2016 | Stoeber et al. |
| 2016/0166184 A1 | 6/2016 | Teng et al. |
| 2016/0213908 A1 | 7/2016 | McAllister et al. |
| 2016/0258945 A1 | 9/2016 | Malima et al. |
| 2016/0270704 A1 | 9/2016 | DeTurk |
| 2016/0296149 A1 | 10/2016 | Polsky et al. |
| 2016/0302687 A1 | 10/2016 | Lee et al. |
| 2016/0370377 A1 | 12/2016 | Ahmad |
| 2017/0003766 A1 | 1/2017 | Budiman |
| 2017/0007813 A1 | 1/2017 | Negi et al. |
| 2017/0035331 A1 | 2/2017 | Parajape et al. |
| 2017/0055835 A1 | 3/2017 | Scherer et al. |
| 2017/0086713 A1 | 3/2017 | Pushpala et al. |
| 2017/0108459 A1 | 4/2017 | Katsuki et al. |
| 2017/0127989 A1 | 5/2017 | Feldman et al. |
| 2017/0128009 A1 | 5/2017 | Pushpala et al. |
| 2017/0164881 A1 | 6/2017 | Fujita et al. |
| 2017/0238851 A1 | 8/2017 | Duhamel et al. |
| 2017/0251958 A1 | 9/2017 | Pushpala et al. |
| 2017/0251959 A1 | 9/2017 | Feldman et al. |
| 2017/0251960 A1 | 9/2017 | Crouther et al. |
| 2017/0311852 A1* | 11/2017 | Morgan ............... A61B 5/1473 |
| 2017/0347925 A1 | 12/2017 | Wang et al. |
| 2017/0347926 A1* | 12/2017 | Farooqui ............... A61B 5/742 |
| 2018/0014787 A1* | 1/2018 | Ganton ................... G01V 3/02 |
| 2018/0116572 A1 | 5/2018 | Simpson et al. |
| 2018/0140235 A1 | 5/2018 | Pushpala et al. |
| 2018/0279929 A1 | 10/2018 | Huang et al. |
| 2018/0317820 A1 | 11/2018 | Pace et al. |
| 2018/0338712 A1 | 11/2018 | Cass et al. |
| 2018/0340203 A1 | 11/2018 | Holmes et al. |
| 2019/0008425 A1 | 1/2019 | Srinivasan et al. |
| 2019/0022365 A1 | 1/2019 | Chowdhury et al. |
| 2019/0029577 A1 | 1/2019 | Koelker et al. |
| 2019/0076075 A1 | 3/2019 | Miller et al. |
| 2019/0090811 A1 | 3/2019 | Reitz et al. |
| 2019/0091455 A1 | 3/2019 | Reitz et al. |
| 2019/0094169 A1 | 3/2019 | Shah et al. |
| 2019/0101551 A1 | 4/2019 | Plaxco et al. |
| 2019/0110724 A1 | 4/2019 | Kamath et al. |
| 2019/0125223 A1 | 5/2019 | Wang et al. |
| 2019/0167167 A1 | 6/2019 | Mitchell et al. |
| 2019/0170739 A1 | 6/2019 | Garner et al. |
| 2019/0201675 A1 | 7/2019 | Miller et al. |
| 2019/0209095 A1 | 7/2019 | Kamath et al. |
| 2019/0223795 A1 | 7/2019 | Patolsky et al. |
| 2019/0224712 A1 | 7/2019 | Petisce et al. |
| 2019/0231263 A1 | 8/2019 | Ribet et al. |
| 2019/0241926 A1 | 8/2019 | Mckinlay et al. |
| 2019/0261907 A1 | 8/2019 | Brister et al. |
| 2019/0274599 A1 | 9/2019 | Polsky et al. |
| 2019/0274600 A1 | 9/2019 | Pesantez et al. |
| 2019/0298210 A1 | 10/2019 | Bennet et al. |
| 2019/0307379 A1 | 10/2019 | Boock et al. |
| 2019/0309433 A1 | 10/2019 | Sattayasamitsathit et al. |
| 2019/0310219 A1 | 10/2019 | Boock |
| 2019/0357827 A1 | 11/2019 | Li et al. |
| 2020/0000387 A1 | 1/2020 | Gerhardt et al. |
| 2020/0029876 A1 | 1/2020 | Brister et al. |
| 2020/0037938 A1 | 2/2020 | Rong et al. |
| 2020/0085341 A1 | 3/2020 | Windmiller |
| 2020/0101286 A1 | 4/2020 | Windmiller et al. |
| 2020/0121902 A1 | 4/2020 | Pushpala et al. |
| 2020/0178853 A1 | 6/2020 | Pushpala et al. |
| 2020/0187778 A1 | 6/2020 | Brister et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2020/0305771 A1 | 10/2020 | Feldman et al. |
| 2020/0330007 A1 | 10/2020 | Garai et al. |
| 2020/0359949 A1 | 11/2020 | Brauker et al. |
| 2020/0390395 A1 | 12/2020 | Pushpala et al. |

(56) References Cited

U.S. PATENT DOCUMENTS

| | | |
|---|---|---|
| 2020/0405234 A1 | 12/2020 | Pushpala et al. |
| 2021/0045663 A1 | 2/2021 | Simpson et al. |
| 2021/0045665 A1 | 2/2021 | Simpson et al. |
| 2021/0045666 A1 | 2/2021 | Simpson et al. |
| 2021/0100452 A1 | 4/2021 | Brister et al. |
| 2021/0100504 A1 | 4/2021 | Pushpala et al. |
| 2021/0100505 A1 | 4/2021 | Pushpala et al. |
| 2021/0183508 A1 | 6/2021 | Parker et al. |
| 2021/0187286 A1 | 6/2021 | Windmiller et al. |
| 2021/0190719 A1 | 6/2021 | LaTour et al. |
| 2021/0236057 A1 | 8/2021 | Pushpala et al. |
| 2021/0321942 A1 | 10/2021 | Pushpala et al. |
| 2021/0345916 A1 | 11/2021 | Boock et al. |
| 2021/0353229 A1 | 11/2021 | Pierart et al. |
| 2021/0379370 A1 | 12/2021 | Windmiller et al. |
| 2021/0386338 A1 | 12/2021 | Zhang et al. |
| 2021/0393201 A1 | 12/2021 | Morelock et al. |
| 2022/0031209 A1 | 2/2022 | Windmiller et al. |
| 2022/0031244 A1 | 2/2022 | Windmiller et al. |
| 2022/0047190 A1 | 2/2022 | Taylor et al. |
| 2022/0054813 A1 | 2/2022 | Pushpala et al. |
| 2022/0054814 A1 | 2/2022 | Pushpala et al. |
| 2022/0104773 A1 | 4/2022 | Lee et al. |
| 2022/0151516 A1 | 5/2022 | Wang et al. |
| 2022/0151518 A1 | 5/2022 | Pushpala et al. |
| 2022/0151519 A1 | 5/2022 | Pushpala et al. |
| 2022/0151558 A1 | 5/2022 | Pushpala et al. |
| 2022/0175278 A1 | 6/2022 | Campbell et al. |
| 2022/0175279 A1 | 6/2022 | Pushpala et al. |
| 2022/0175282 A1 | 6/2022 | Hoss et al. |
| 2022/0214300 A1 | 7/2022 | Wang et al. |
| 2022/0225901 A1 | 7/2022 | Chapman et al. |
| 2022/0233107 A1 | 7/2022 | Pushpala et al. |
| 2022/0249189 A1 | 8/2022 | Choi et al. |
| 2022/0257181 A1 | 8/2022 | Wang et al. |
| 2022/0298291 A1 | 9/2022 | Shin et al. |
| 2022/0322975 A1 | 10/2022 | Baker et al. |
| 2022/0322977 A1 | 10/2022 | Simpson et al. |
| 2022/0361776 A1 | 11/2022 | Wang et al. |
| 2022/0370011 A1 | 11/2022 | Windmiller et al. |
| 2023/0003725 A1 | 1/2023 | Wang et al. |
| 2023/0012662 A1 | 1/2023 | Tehrani et al. |
| 2023/0074798 A1 | 3/2023 | Tangney et al. |
| 2023/0094419 A1 | 3/2023 | Mansfield, III et al. |
| 2023/0099617 A1 | 3/2023 | Mansfield, III et al. |
| 2023/0137258 A1 | 5/2023 | Windmiller |
| 2023/0190147 A1 | 6/2023 | Campbell et al. |
| 2023/0256220 A1 | 8/2023 | Mansfield et al. |
| 2023/0301552 A1 | 9/2023 | Mallires et al. |
| 2023/0310823 A1 | 10/2023 | Mansfield et al. |
| 2023/0414102 A1 | 12/2023 | Allen et al. |
| 2024/0008777 A1 | 1/2024 | Fuchs et al. |
| 2024/0081740 A1 | 3/2024 | Windmiller et al. |
| 2024/0164719 A1 | 5/2024 | Campbell et al. |
| 2024/0252115 A1 | 8/2024 | Tangney et al. |
| 2024/0315614 A1 | 9/2024 | Campbell et al. |
| 2024/0341636 A1 | 10/2024 | Yang et al. |
| 2024/0366125 A1 | 11/2024 | Alonso-Soski et al. |
| 2024/0366149 A1 | 11/2024 | Kendall et al. |
| 2024/0382157 A1 | 11/2024 | Windmiller et al. |
| 2024/0408366 A1 | 12/2024 | Mansfield et al. |
| 2024/0423526 A1 | 12/2024 | Windmiller et al. |
| 2025/0000395 A1 | 1/2025 | Brister et al. |
| 2025/0049397 A1 | 2/2025 | Campbell et al. |
| 2025/0213859 A1 | 7/2025 | Windmiller et al. |

FOREIGN PATENT DOCUMENTS

| | | |
|---|---|---|
| CN | 112617822 A | 4/2021 |
| CN | 113717955 A | 11/2021 |
| DE | 102015209669 A1 | 12/2016 |
| EP | 1006868 B1 | 6/2004 |
| EP | 1 372 602 B1 | 4/2007 |
| EP | 1792565 B1 | 10/2008 |
| EP | 1 187 653 B1 | 3/2010 |
| EP | 2 898 821 B1 | 12/2017 |
| EP | 3364183 A1 | 8/2018 |
| EP | 3 381 370 A1 | 10/2018 |
| EP | 3829418 B1 | 11/2024 |
| EP | 3829437 B1 | 11/2024 |
| EP | 4009865 B1 | 11/2024 |
| EP | 4482372 A1 | 1/2025 |
| JP | H0222552 A | 1/1990 |
| JP | H-02-031741 A | 2/1990 |
| JP | H067324 A | 1/1994 |
| JP | H-07-275227 A | 10/1995 |
| JP | 2003-038464 A | 2/2003 |
| JP | 2003-038465 A | 2/2003 |
| JP | 2003111742 A | 4/2003 |
| JP | 2004180773 A | 7/2004 |
| JP | 2005-087613 A | 4/2005 |
| JP | 2006-510467 A | 4/2005 |
| JP | 2005-525141 A | 8/2005 |
| JP | 2005-322591 A | 11/2005 |
| JP | 2008-512162 A | 4/2008 |
| JP | 2008-540013 A | 11/2008 |
| JP | 2008544763 A | 12/2008 |
| JP | 2010523167 A | 7/2010 |
| JP | 2013506847 A | 2/2013 |
| JP | 2013521942 A | 6/2013 |
| JP | 2014533523 A | 12/2014 |
| JP | 2017108763 A | 6/2017 |
| JP | 2019107040 A | 7/2019 |
| JP | 2019526332 A | 9/2019 |
| JP | 2019205852 A | 12/2019 |
| JP | 2020170011 A | 10/2020 |
| JP | 2022501100 A | 1/2022 |
| JP | 2022508575 A | 1/2022 |
| KR | 10-2016-0108111 A | 9/2016 |
| WO | WO-00/74763 A2 | 12/2000 |
| WO | WO-00/74763 A3 | 12/2000 |
| WO | WO-2006/060106 A1 | 6/2006 |
| WO | WO2006093422 | 9/2006 |
| WO | WO-2006/116242 A2 | 11/2006 |
| WO | WO-2006/116242 A3 | 11/2006 |
| WO | WO-2007/040938 A1 | 4/2007 |
| WO | WO2009034313 | 3/2009 |
| WO | WO2009064164 | 5/2009 |
| WO | WO-2009/124095 A1 | 10/2009 |
| WO | WO-2010/014959 A2 | 2/2010 |
| WO | WO-2010/014959 A3 | 2/2010 |
| WO | WO-2010/022252 A2 | 2/2010 |
| WO | WO-2010/022252 A3 | 2/2010 |
| WO | WO-2010/045247 A1 | 4/2010 |
| WO | WO-2010/059276 A1 | 5/2010 |
| WO | WO2010120364 | 10/2010 |
| WO | WO-2011/056095 A1 | 5/2011 |
| WO | WO2012020332 | 2/2012 |
| WO | WO-2012/142625 A2 | 10/2012 |
| WO | WO-2012/142625 A3 | 10/2012 |
| WO | WO2013058879 | 4/2013 |
| WO | WO-2014120114 A1 | 8/2014 |
| WO | WO2015073459 | 5/2015 |
| WO | WO-2016189301 A1 | 12/2016 |
| WO | WO-2017/129980 A1 | 8/2017 |
| WO | WO-2017/189707 A1 | 11/2017 |
| WO | WO-2018/017196 A1 | 1/2018 |
| WO | WO-2018/071265 A1 | 4/2018 |
| WO | WO-2018/170363 A1 | 9/2018 |
| WO | WO2018164886 | 9/2018 |
| WO | WO-2019046333 A1 | 3/2019 |
| WO | WO-2019/156934 A1 | 8/2019 |
| WO | WO-2019/222615 A1 | 11/2019 |
| WO | WO-2019/239258 A1 | 12/2019 |
| WO | WO-2020/023804 A1 | 1/2020 |
| WO | WO-2020069565 A1 | 4/2020 |
| WO | WO-2020069567 A1 | 4/2020 |
| WO | WO-2020069570 A1 | 4/2020 |
| WO | WO-2020117918 A1 | 6/2020 |
| WO | WO-2021/015389 A1 | 1/2021 |
| WO | WO-2021/025260 A1 | 2/2021 |
| WO | WO-2021062475 A1 | 4/2021 |
| WO | WO-2021086690 A1 | 5/2021 |
| WO | WO-2021118124 A1 | 6/2021 |

(56) References Cited

FOREIGN PATENT DOCUMENTS

| WO | WO-2021118431 A1 | 6/2021 |
| WO | WO-2021216186 A2 | 10/2021 |
| WO | WO-2021216186 A9 | 12/2021 |
| WO | WO-2022026764 A1 | 2/2022 |
| WO | WO-2022066985 A1 | 3/2022 |
| WO | WO-2022066992 A1 | 3/2022 |
| WO | WO-2022090741 A1 | 5/2022 |
| WO | WO-2022136785 A1 | 6/2022 |
| WO | WO-2022240700 A1 | 11/2022 |
| WO | WO-2023055755 A1 | 4/2023 |
| WO | WO-2023064877 A1 | 4/2023 |
| WO | WO-2023133468 A1 | 7/2023 |
| WO | WO-2023229662 A2 | 11/2023 |
| WO | WO-2024000015 A1 | 1/2024 |
| WO | WO-2024010827 A1 | 1/2024 |
| WO | WO-2024163950 A2 | 8/2024 |
| WO | WO-2024238798 A1 | 11/2024 |
| WO | WO-2025144429 A2 | 7/2025 |

OTHER PUBLICATIONS

Abbot press release (2020). "New late-breaking data show use of abbott's Freestyle® Libre System significantly reduces HBA1C levels in people with type 2 diabetes using insulin or not," 3 pages.

American Diabetes Association® Press Release (2020). "American Diabetes Association® Applauds policymakers' Focus on Addressing High Costs of Insulin for Seven Million Americans," 4 pages.

Bantle, J.P. et al. (1997). "Glucose measurement in patients with diabetes mellitus with dermal interstitial fluid," J. Lab. Clin. Med. 130:436-441.

Beckles, G.L. et al. (2016). "Disparities in the prevalence of diagnosed diabetes—United States, 1999-2002 and 2011-2014," MMWR 65:1265-1269.

Cao, J. et al. (2017). "Validation of capillary blood analysis and capillary testing mode on the epoc Point of Care system," Pract. Lab. Med. 9:24-27.

Castle, J.R. et al. (2012). "The accuracy benefit of multiple amperometric glucose sensors in people with type 1 diabetes," Diabetes Care 35:706-710.

Chang, H. et al. (2017). "A swellable microneedle patch to rapidly extract skin interstitial fluid for timely metabolic analysis," Adv. Mater. 29:1702243.

Dexcom (2020). Analyst Day Presentation, 27 total pages.

Dexcom (2020). Analyst Day Presentation, 19 total pages.

Diabetes Care (2021). "7. Diabetes Technology: Standards of Medical Care in Diabetes—2021," Diabetes Care 44(Supplement 1):S85-S99.

Donnelly, R.F. et al. (2007). "Microstructured Devices for Transdermal Drug Delivery and Minimally-Invasive Patient Monitoring," Recent Patents on Drug Delivery & Formulation 1:195-200.

Extended European Search Report mailed on May 8, 2015, for EP Application No. 12 842 020.5, filed on Aug. 31, 2012, 7 pages.

Fang, M. et al. (2021). "Trends in Diabetes Treatment and Control in U.S. Adults, 1999-2018," N. Engl. Med. 384:2219-2228.

Final Office Action mailed on Aug. 19, 2016, for U.S. Appl. No. 14/965,755, filed Dec. 10, 2015, 17 pages.

Final Office Action mailed on Nov. 28, 2016, for U.S. Appl. No. 14/342,536, filed Jul. 30, 2014, 34 pages.

Final Office Action mailed on May 18, 2018, for U.S. Appl. No. 15/687,145, filed Aug. 25, 2017, 23 pages.

Final Office Action mailed on Dec. 7, 2020, for U.S. Appl. No. 15/961,793, filed on Apr. 24, 2018, 13 pages.

Final Office Action mailed on Jun. 9, 2021, for U.S. Appl. No. 16/169,939, filed on Oct. 24, 2018, 24 pages.

Final Office Action mailed on Sep. 23, 2021, for U.S. Appl. No. 15/913,709, filed Mar. 6, 2018, 17 pages.

Final Office Action mailed on May 9, 2022, for U.S. Appl. No. 17/389,153, filed Jul. 29, 2021, 17 pages.

French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.

Gittard, S.D. et al. (2009). "Fabrication of Polymer Microneedles Using a Two-Photon Polymerization and Micromolding Process," J. Diabetes Sci. Technol. 3:304-311.

Grady, M. et al. (2017). "Examining the Impact of a Novel Blood Glucose Monitor With Color Range Indicator on Decision-Making in Patients With Type 1 and Type 2 Diabetes and its Association With Patient Numeracy Level," JMIR Diabetes 2:e24.

Grady, M. et al. (2018). "Use of Blood Glucose Meters Featuring Color Range Indicators Improves Glycemic Control in Patients With Diabetes in Comparison to Blood Glucose Meters Without Color (ACCENTS Study)," J. Diab. Sci. Tech. 12:1211-1219.

Groenendaal, W. et al. (2008). "Modeling Glucose and Water Dynamics in Human Skin," Diab. Tech. Therap. 10:283-293.

International Search Report mailed on Feb. 4, 2021, for PCT Application No. PCT/US2020/056517, filed on Oct. 20, 2020, 2 pages.

International Search Report mailed on Sep. 10, 2020, for PCT Application No. PCT/US2020/037379, filed on Jun. 12, 2020, 2 pages.

International Search Report mailed on Dec. 30, 2021, for PCT Application No. PCT/US2021/043786, filed on Jul. 29, 2021, 7 pages.

International Search Report mailed on Jun. 27, 2013, for PCT Application No. PCT/US2012/053544, filed on Aug. 31, 2012, 4 pages.

Jeon, G. et al. (2011). "Electrically Actuatable Smart Nanoporous Membrane for Pulsatile Drug Release," Nano Lett. 11:1284-1288.

Jina, A et al. (2014). "Design, development, and evaluation of a novel microneedle array-based continuous glucose monitor," J. Diabetes Sci. Technol. 8:483-487.

Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.

Karter, A.J. et al. (2021). "Association of Real-time Continuous Glucose Monitoring With Glycemic Control and Acute Metabolic Events Among Patients With Insulin-Treated Diabetes," JAMA 325:2273-2284.

Lhernould, M.S. et al. (2015). "Review of Patents for Microneedle Application Devices Allowing Fluid Injections Through the Skin," Recent Patents on Drug Delivery & Formulation 9:146-157.

Malitesta et al. (1990). "Glucose fast-response amperometric sensor based on glucose oxidase immobilized in an electropolymerized poly(o-phenylenediamine) film," Anal. Chem. 62:2735-2740.

Martens, T. et al. (2021). "Effect of Continuous Glucose Monitoring on Glycemic Control in Patients With Type 2 Diabetes Treated With Basal Insulin a Randomized Clinical Trial," JAMA 325:2262-2272.

McClatchey, P.M. et al. (2019). "Fibrotic Encapsulation is the Dominant Source of Continuous Glucose Monitor Delays," Diabetes 68:1892-1901.

Miller, P.R. et al. (2011). "Integrated carbon fiber electrodes within hollow polymer microneedles for transdermal electrochemical sensing," BioMicrofluidics 5(1):013415.

Neerken, S. et al. (2004). "Characterization of age-related effects in human skin: A comparative study that applies confocal laser scanning microscopy and optical coherence tomography," J. Biomed. Optics 9:274-281.

Non-Final Office Action mailed on Mar. 10, 2016, for U.S. Appl. No. 14/965,755, filed Dec. 10, 2015, 15 pages.

Non-Final Office Action mailed on Mar. 30, 2016, for U.S. Appl. No. 14/342,536, filed Jul. 30, 2014, 31 pages.

Non-Final Office Action mailed on Mar. 9, 2017, for U.S. Appl. No. 14/965,755, filed Dec. 10, 2015, 17 pages.

Non-Final Office Action mailed on Apr. 6, 2017, for U.S. Appl. No. 14/342,536, filed Jul. 30, 2014, 32 pages.

Non-Final Office Action mailed on Nov. 1, 2017, for U.S. Appl. No. 15/687,145, filed Aug. 25, 2017, 19 pages.

Non-Final Office Action mailed on Jan. 19, 2018, for U.S. Appl. No. 14/843,926, filed Sep. 2, 2015, 11 pages.

Non-Final Office Action mailed on Apr. 13, 2020, for U.S. Appl. No. 15/961,793, filed Apr. 24, 2018, 13 pages.

(56)        References Cited

OTHER PUBLICATIONS

Non-Final Office Action mailed on Sep. 3, 2020, for U.S. Appl. No. 16/169,939, filed Oct. 24, 2018, 19 pages.
Non-Final Office Action mailed on Sep. 16, 2020, for U.S. Appl. No. 15/913,709, filed Mar. 6, 2018, 15 pages.
Non-Final Office Action mailed on Nov. 4, 2021, for U.S. Appl. No. 16/169,939, filed Oct. 24, 2018, 20 pages.
Non-Final Office Action mailed on Nov. 29, 2021, for U.S. Appl. No. 17/389,153, filed Jul. 29, 2021, 14 pages.
Non-Final Office Action mailed on Apr. 8, 2022, for U.S. Appl. No. 17/650,056, filed Feb. 4, 2022, 14 pages.
Non-Final Office Action mailed on May 13, 2022, for U.S. Appl. No. 15/913,709, filed Mar. 6, 2018, 20 pages.
Notice of Allowance mailed on Jul. 6, 2017, for U.S. Appl. No. 14/965,755, filed Dec. 10, 2015, 12 pages.
Notice of Allowance mailed on Jul. 12, 2017, for U.S. Appl. No. 14/342,536, filed Jul. 30, 2014, 14 pages.
Notice of Allowance mailed on Feb. 13, 2018, for U.S. Appl. No. 14/843,926, filed Sep. 2, 2015, 8 pages.
Notice of Allowance mailed on Aug. 24, 2018, for U.S. Appl. No. 15/687,145, filed Aug. 25, 2017, 7 pages.
Notice of Allowance mailed on May 25, 2021, for U.S. Appl. No. 15/961,793, filed Apr. 24, 2018, 11 pages.
Polonsky, W.H. et al. (2011). "A survey of blood glucose monitoring in patients with type 2 diabetes: Are recommendations from health care professionals being followed?" Curr. Med. Res. & Opinion 27:31-37.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sachdeva, V. et al. (2011). "Microneedles and their applications," Recent Patents on Drug Delivery & Formulation 5:95-132.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.
Singh, T.R.R. et al. (2010). "Microporation techniques for enhanced delivery of therapeutic agents," Recent Patents on Drug Delivery & Formulation 4:1-17.
Texas Instruments (Sep. 2007). Data sheet for a LMP2234 quad micropower, 1.6V, precision, operational amplifier with CMOS input, Sep. 2007, revised Mar. 2013.
Windmiller, J.R. (2012). "Molecular scale biocomputing: An enzyme logic approach," University of California, San Diego, A dissertation submitted in partial satisfaction of the requirements for the degree Doctor of Philosophy in Electrical Engineering (Photonics), 78 total pages.
Windmiller, J.R. et al. (2011). "Bicomponent microneedle array biosensor for minimally-invasive glutamate monitoring," Electroanalysis 23:2302-2309.
Windmiller, J.R. et al. (2011). "Microneedle array-based carbon paste amperometric sensors and biosensors," Analyst 136: 1846-1851.
Written Opinion of the International Searching Authority mailed on Feb. 4, 2021, for PCT Application No. PCT/US2020/056517, filed on Oct. 20, 2020, 5 pages.
Written Opinion of the International Searching Authority mailed on Sep. 10, 2020, for PCT Application No. PCT/US2020/037379, filed on Jun. 12, 2020, 4 pages.
Written Opinion of the International Searching Authority mailed on Dec. 30, 2021, for PCT Application No. PCT/US2021/043786, filed on Jul. 29, 2021, 10 pages.
Written Opinion of the International Searching Authority mailed on Jun. 27, 2013, for PCT Application No. PCT/US2012/053544, filed on Aug. 31, 2012, 15 pages.
Extended European Search Report mailed on Oct. 27, 2022, for EP Application No. 21 850 331.6, filed on Jul. 29, 2021, 8 pages.

Final Office Action mailed on Oct. 27, 2022, for U.S. Appl. No. 15/913,709, filed Mar. 6, 2018, 21 pages.
International Search Report mailed on Sep. 30, 2021, for PCT Application No. PCT/US2021/040385, filed on Jul. 2, 2021, 2 pages.
International Search Report mailed on Aug. 29, 2022, for PCT Application No. PCT/US2022/028196, filed on May 6, 2022, 2 pages.
Mohan, A.M. (2017). "Continuous minimally-invasive alcohol monitoring using microneedle sensor arrays," Biosensors and Bioelectronics 91:574-579.
Notice of Allowance mailed on Sep. 12, 2022, for U.S. Appl. No. 17/389,153, filed Jul. 29, 2021, 8 pages.
Written Opinion of the International Searching Authority mailed on Sep. 30, 2021, for PCT Application No. PCT/US2021/040385, filed on Jul. 2, 2021, 2 pages.
Written Opinion of the International Searching Authority mailed on Aug. 29, 2022, for PCT Application No. PCT/US2022/028196, filed on May 6, 2022, 5 pages.
Al Hayek et al., "Patient Satisfaction and Clinical Efficacy of Novel Blood Glucose Meters Featuring Color Range Indicators in Patients With Type 2 Diabetes: A Prospective Study" Cureus (2020) Oct. 27; 12(10):e11195. 8 pages. doi: 10.7759/cureus.11195.
Allen et al., "Continuous glucose monitoring counseling improves physical activity behaviors of individuals with type 2 diabetes: A randomized clinical trial" Diabetes Res Clin Pract. (2008) Jun. 80(3): 371-379. doi:10.1016/j.diabres.2008.01.006.
Barrett et al., "Risk for Newly Diagnosed Diabetes 30 Days After SARS-CoV-2 Infection Among Persons Aged 18 Years—United States, Mar. 1, 2020-Jun. 28, 2021" MMWR Morb Mortal Wkly Rep. (2022) Jan. 14; 71(2):59-65. doi: 10.15585/mmwr.mm7102e2.
Brown, "Design of Electronics for Wearable Electrochemical Sensors", University of California, San Diego, Master's Thesis (2019) 48 pgs.
Centers for Disease Control, "National Diabetes Statistics Report 2020 Estimates of Diabetes and Its Burden in the United States" (2020) 32 pages.
Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.
Ehrhardt et al., "Behavior Modification in Prediabetes and Diabetes: Potential Use of Real-Time Continuous Glucose Monitoring" Journal of Diabetes Science and Technology Mar. 2019; 13(2):271-275.
Ehrhardt et al., "Continuous Glucose Monitoring as a Behavior Modification Tool" Clin Diabetes. (2020) Apr. 38(2):126-131. doi: 10.2337/cd19-0037.
Ehrhardt et al., "The Effect of Real-Time Continuous Glucose Monitoring on Glycemic Control in Patients with Type 2 Diabetes Mellitus" Journal of Diabetes Science and Technology May 2011; 5(3):668-675.
Extended European Search Report mailed on Mar. 30, 2023, for European Application No. EP20881425.1, 8 pages.
Fonda et al., "The Cost-Effectiveness of Real-Time Continuous Glucose Monitoring (RT-CGM) in Type 2 Diabetes" Journal of Diabetes Science and Technology (2016) 10(4): 898-904.
Han et al., "The End of the Road for the YSI 2300 Analyzer: Where Do We Go Now?" Journal of Diabetes Science and Technology (2020) 14(3):595-600.
Han et al., "The YSI 2300 Analyzer Replacement Meeting Report" Journal of Diabetes Science and Technology (2020) 14(3):679-686.
Non-Final Office Action mailed on Jan. 27, 2023, for U.S. Appl. No. 17/971,415, filed Oct. 21, 2022, 15 pages.
Non-Final Office Action mailed on Feb. 16, 2023, for U.S. Appl. No. 17/738,990, 9 pages.
Non-Final Office Action mailed on Mar. 9, 2023, for U.S. Appl. No. 17/389,156, filed Jul. 29, 2021, 24 pages.
Non-Final Office Action mailed on May 2, 2023, for U.S. Appl. No. 15/913,709, filed Mar. 6, 2018, 18 pages.
Non-Final Office Action mailed on May 24, 2023, for U.S. Appl. No. 18/086,543, filed Dec. 21, 2022, 19 pages.
Non-Final Office Action mailed on Jun. 2, 2023, for U.S. Appl. No. 17/367,274, filed Jul. 2, 2021, 27 pages.

(56)　　　　References Cited

OTHER PUBLICATIONS

Non-Final Office Action mailed on Jun. 20, 2023, for U.S. Appl. No. 17/073,331, filed Oct. 17, 2020, 10 pages.
Notice of Allowance mailed on Jun. 12, 2023, for U.S. Appl. No. 17/971,415, filed Oct. 21, 2022, 14 pages.
Notice of Allowance mailed on Jun. 12, 2023, for U.S. Appl. No. 17/738,990, filed May 6, 2022, 7 pages.
Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.
Swedish Search Report mailed on Feb. 3, 2023 for SE Application No. 2350067-1, 7 pages.
Turner et al., "Intensive blood-glucose control with sulphonylureas or insulin compared with conventional treatment and risk of complications in patients with type 2 diabetes (UKPDS 33)" The Lancet (1998) Sep; 352(9131):837-853.
Vigersky et al., "Short- and Long-Term Effects of Real-Time Continuous Glucose Monitoring in Patients with Type 2 Diabetes" Diabetes Care Jan. 2012; 35:32-38.
Wolicki et al., "Epidemiology and Prevention of Vaccine-Preventable Diseases: Chapter 6: Vaccine Administration" Centers for Disease Control and Prevention (2021) 17 pages.
World Health Organization, "Diabetes", Sep. 16, 2022, 5 pages.
Young et al., "Glucose Self-monitoring in Non-Insulin-Treated Patients With Type 2 Diabetes in Primary Care Settings: A Randomized Trial" JAMA Intern Med. Jul. 2017; 177(7):920-929.
Final Office Action mailed on Nov. 27, 2023, for U.S. Appl. No. 17/389,156, filed Jul. 29, 2021, 29 pages.
Final Office Action mailed on Aug. 29, 2023, for U.S. Appl. No. 18/086,543, filed Dec. 21, 2022, 17 pages.
Non-Final Office Action mailed on Dec. 13, 2023, for U.S. Appl. No. 18/086,543, filed Dec. 21, 2022, 16 pages.
Notice of Allowance mailed on Sep. 25, 2023, for U.S. Appl. No. 17/971,415, filed Oct. 21, 2022, 8 pages.
Notice of Allowance mailed on Sep. 26, 2023, for U.S. Appl. No. 17/738,990, filed May 6, 2022, 7 pages.
Notice of Allowance mailed on Dec. 20, 2023, for U.S. Appl. No. 17/349,234, filed Jun. 16, 2021, 13 pages.
Office Action and Swedish Search Report mailed on Oct. 17, 2023, for SE Application No. 2251496-2, 8 pages.
Supplementary European Search Report mailed on Oct. 9, 2023, for EP Application No. 22808101.4, 4 pages.
American Diabetes Association, "Diabetes and Emotional Health: A Practical Guide for Health Professionals Supporting Adults with Type 1 and Type 2 Diabetes" U.S. Edition (2021), 214 pages.
American Diabetes Association Professional Practice Committee, "6. Glycemic Goals and Hypoglycemia: Standards of Care in Diabetes-2024" Diabetes Care Jan. 1, 2024; 47(Suppl 1):S111-S125.
American Diabetes Association Professional Practice Committee, "7. Diabetes Technology: Standards of Medical Care in Diabetes-2022" Diabetes Care Jan. 1, 2022; 45(Suppl 1):S97-S112.
Centers for Disease Control, "National Diabetes Statistics Report" May 2024, 16 pages.
Chen et al., "Electrochemically Mediated Electrodeposition/ Electropolymerization to Yield a Glucose Microbiosensor with Improved Characteristics" Anal. Chem. (2002) 74:368-372.
Diabetes Control and Complications Trial Research Group, "The effect of intensive treatment of diabetes on the development and progression of long-term complications in insulin-dependent diabetes mellitus" N Engl J Med (1993) Sep. 30; 329(14):977-986.
Elsayed et al., "2. Classification and Diagnosis of Diabetes: Standards of Care in Diabetes-2023" Diabetes Care Jan. 1, 2023; 46(Suppl 1):S19-S40.
Extended European Search Report for European Application No. 23218205.5 dated Jun. 11, 2024, 7 pages.
Extended European Search Report for European Application No. EP20898007.8 dated Nov. 29, 2023, 9 pages.

Extended European Search Report for European Application No. EP21837561.6 dated Jun. 21, 2024, 7 pages.
Final Office Action mailed on Feb. 1, 2024, for U.S. Appl. No. 17/073,331, filed Oct. 17, 2020, 12 pages.
Final Office Action mailed on Mar. 15, 2024, for U.S. Appl. No. 17/367,274, filed Jul. 2, 2021, 33 pages.
International Search Report and Written Opinion for PCT Application No. PCT/US2020/064700, mail date Mar. 9, 2021, 11 pages.
International Search Report and Written Opinion mailed on Feb. 6, 2024, for International Application No. PCT/US2022/078819, filed on Oct. 27, 2022, 13 pages.
Invitation to pay additional fees for International Application No. PCT/US2024/014324, dated Jul. 30, 2024, 16 pages.
Mendes-Soares et al., "Assessment of a Personalized Approach to Predicting Postprandial Glycemic Responses to Food Among Individuals Without Diabetes" JAMA Network Open Feb. 1, 2019; 2(2):e188102. 13 pages.
Miller et al., "Hypoglycemia in patients with type 2 diabetes mellitus" Arch Intern Med Jul. 9, 2001; 161(13):1653-1659.
Newton et al., "Diabetic ketoacidosis in type 1 and type 2 diabetes mellitus: clinical and biochemical differences" Arch Intern Med Sep. 27, 2004; 164(17):1925-1931.
Non-Final Office Action for U.S. Appl. No. 17/389,156 dated Apr. 16, 2024, 28 pages.
Non-Final Office Action for U.S. Appl. No. 18/630,936 mailed Jun. 13, 2024, 19 pages.
Non-Final Office Action mailed on Jan. 26, 2024, for U.S. Appl. No. 15/913,709, filed Mar. 6, 2018, 20 pages.
Non-Final Office Action mailed on May 24, 2024, for U.S. Appl. No. 18/527,128, filed Dec. 1, 2023, 17 pages.
Notice of Allowance (Corrected) mailed on Apr. 19, 2024, for U.S. Appl. No. 18/086,543, filed Dec. 21, 2022, 4 pages.
Notice of Allowance (Corrected) mailed on Jan. 25, 2024, for U.S. Appl. No. 17/349,234, filed Jun. 16, 2021, 4 pages.
Notice of Allowance (Corrected) mailed on Mar. 18, 2024, for U.S. Appl. No. 17/349,234, filed Jun. 16, 2021, 9 pages.
Notice of Allowance mailed on Apr. 10, 2024, for U.S. Appl. No. 18/086,543, filed Dec. 21, 2022, 10 pages.
Notice of Allowance mailed on Jun. 11, 2024, for U.S. Appl. No. 15/913,709, filed Mar. 6, 2018, 9 pages.
Notice of Allowance mailed on Mar. 21, 2024, for U.S. Appl. No. 18/086,543, filed Dec. 21, 2022, 6 pages.
Notice of Allowance mailed on Mar. 4, 2024, for U.S. Appl. No. 18/086,543, filed Dec. 21, 2022, 10 pages.
Segel et al., "Hypoglycemia-associated autonomic failure in advanced type 2 diabetes" Diabetes Mar. 2002; 51(3):724-733.
Shivers et al., "Turn it off!: diabetes device alarm fatigue considerations for the present and the future" J Diabetes Sci Technol May 1, 2013; 7(3):789-794.
Tanenbaum et al., "Diabetes Device Use in Adults With Type 1 Diabetes: Barriers to Uptake and Potential Intervention Targets" Diabetes Care Feb. 2017; 40(2):181-187.
UK Prospective Diabetes Study (UKPDS) Group, "Intensive blood-glucose control with sulphonylureas or insulin compared with conventional treatment and risk of complications in patients with type 2 diabetes (UKPDS 33)" Lancet Sep. 12, 1998; 352(9131):837-853.
Ward et al., "A Wired-Based Dual-Analyte Sensor for Glucose and Lactate: In Vitro and In Vivo Evaluation" Diabetes Technology and Therapeutics Jun. 2004; 6(3):389-401.
Battelino et al., "Continuous glucose monitoring and metrics for clinical trials: an international consensus statement" Lancet Diabetes Endocrinol (2023) 11:42-57.
Clutter et al., "Epinephrine plasma metabolic clearance rates and physiologic thresholds for metabolic and hemodynamic actions in man" J Clin Invest. (1980) 66(1):94-101.
Czupryniak et al., "Ambulatory Glucose Profile (AGP) Report in Daily Care of Patients with Diabetes: Practical Tips and Recommendations" Diabetes Ther (2022) 13:811-821.
Donnelly et al., "Microneedle Arrays Allow Lower Microbial Penetration Than Hypodermic Needles In Vitro" Pharmaceutical Research (2009) 26(11):2513-2522.

(56) References Cited

OTHER PUBLICATIONS

Eddy et al., "The modification of enzyme electrode properties with non-conducting electropolymerised films" Biosensors & Bioelectronics (1995) 10:831-839.

Extended European search report for European Application No. 25151041.8 mailed May 27, 2025, 7 pages.

Fayfman et al., "Management of Hyperglycemic Crises: Diabetic ketoacidosis and hyperglycemic hyperosmolar state" Med Clin North Am. May 2017; 101(3):587-606.

Final Office Action for U.S. Appl. No. 17/073,331 mailed Dec. 17, 2024, 13 pages.

Final Office Action for U.S. Appl. No. 17/650,056 mailed on Feb. 14, 2025, 34 pages.

Final Office Action for U.S. Appl. No. 18/527,128 mailed Sep. 6, 2024, 19 pages.

Final Office Action for U.S. Appl. No. 18/630,936 mailed Sep. 20, 2024, 16 pages.

Final Office Action mailed on Jul. 15, 2022, for U.S. Appl. No. 17/650,056, filed Feb. 4, 2022, 25 pages.

Final Office Action mailed on Sep. 7, 2023, for U.S. Appl. No. 17/650,056, filed Feb. 4, 2022, 29 pages.

Gao et al., "Simultaneous detection of glucose, uric acid and cholesterol using flexible microneedle electrode array-based biosensor and multi-channel portable electrochemical analyzer" Sensors and Actuators B: Chemical (2019) 287:102-110.

Ghimire et al., "Ketoacidosis" StatPearls Publishing, Jan. 2024, NCBI Bookshelf, 8 pages.

Heinemann, "Interferences With CGM Systems: Practical Relevance?" Journal of Diabetes Science and Technology (2022) vol. 16(2) 271-274.

Henry et al., "Microfabricated microneedles: a novel approach to transdermal drug delivery" Journal of Pharmaceutical Sciences Aug. 1, 1998; 87(8):922-925.

International Search Report and Written Opinion for PCT Application No. PCT/US2024/014324 mailed Sep. 20, 2024, 22 pages.

Maahs et al., "Effect of Acetaminophen on CGM Glucose in an Outpatient Setting" Diabetes Care (2015) 38:e158-e159.

Nguyen et al., "Human studies with microneedles for evaluation of their efficacy and safety" Expert Opinion on Drug Delivery (2018) 15:3, 235-245.

Non-Final Office Action for U.S. Appl. No. 17/073,331 mailed Aug. 28, 2024, 13 pages.

Non-Final Office Action for U.S. Appl. No. 17/073,331 mailed Jul. 16, 2025, 21 pages.

Non-Final Office Action for U.S. Appl. No. 17/389,156 mailed Jan. 22, 2025, 17 pages.

Non-Final Office Action for U.S. Appl. No. 17/757,216 mailed on Mar. 26, 2025, 14 pages.

Non-Final Office Action for U.S. Appl. No. 18/050,450 mailed on Aug. 13, 2025, 9 pages.

Non-Final Office Action for U.S. Appl. No. 18/431,808 mailed Nov. 27, 2024, 16 pages.

Non-Final Office Action for U.S. Appl. No. 18/630,936 mailed on Dec. 12, 2024, 18 pages.

Non-Final Office Action for U.S. Appl. No. 18/824,598 mailed Nov. 4, 2024, 14 pages.

Non-Final Office Action for U.S. Appl. No. 18/824,598 mailed on Dec. 23, 2024, 27 pages.

Non-Final Office Action for U.S. Appl. No. 18/926,029 mailed on Dec. 12, 2024, 10 pages.

Non-Final Office Action for U.S. Appl. No. 19/213,907 mailed Aug. 8, 2025, 12 pages.

Non-Final Office Action for U.S. Appl. No. 19/258,472 mailed on Aug. 12, 2025, 29 pages.

Non-Final Office Action mailed on Jul. 30, 2024, for U.S. Appl. No. 17/650,056, filed Feb. 4, 2022, 32 pages.

Non-Final Office Action mailed on Mar. 29, 2023, for U.S. Appl. No. 17/650,056, filed Feb. 4, 2022, 27 pages.

Notice of Allowance for U.S. Appl. No. 17/389,156 mailed Dec. 27, 2024, 6 pages.

Notice of Allowance for U.S. Appl. No. 17/389,156 mailed Nov. 20, 2024, 5 pages.

Notice of Allowance for U.S. Appl. No. 17/389,156 mailed Sep. 25, 2024, 12 pages.

Notice of Allowance for U.S. Appl. No. 18/431,808 mailed Feb. 20, 2025, 7 pages.

Notice of Allowance for U.S. Appl. No. 18/527,128 mailed Feb. 26, 2025, 9 pages.

Notice of Allowance for U.S. Appl. No. 18/630,936 mailed Jul. 1, 2025, 8 pages.

Notice of Allowance for U.S. Appl. No. 18/824,598 mailed Apr. 4, 2025, 9 pages.

Notice of Allowance for U.S. Appl. No. 18/926,029 mailed Mar. 5, 2025, 8 pages.

Ohashi et al., "Analgesic Effect of Acetaminophen: A Review of Known and Novel Mechanisms of Action" Front Pharmacol. Nov. 30, 2020;11:580289, 6 pages.

Prausnitz, "Engineering Microneedle Patches for Vaccination and Drug Delivery to Skin" Annu. Rev. Chem. Biomol. Eng. (2017) 8:177-200.

Samant et al., "Mechanisms of sampling interstitial fluid from skin using a microneedle patch," Proc. Natl Acad. Sci. U.S.A. (2018) 115(8):4583-4588.

Vicente-Perez et al., "Repeat application of microneedles does not alter skin appearance or barrier function and causes no measurable disturbance of serum biomarkers of infection, inflammation or immunity in mice in vivo" European Journal of Pharmaceutics and Biopharmaceutics (2017) 117:400-407.

Yue et al., "Evaluation of a 12-Hour Sustained-Release Acetaminophen (Paracetamol) Formulation: A Randomized, 3-Way Crossover Pharmacokinetic and Safety Study in Healthy Volunteers" Clinical Pharmacology in Drug Development (2018) 7(1) 95-101.

* cited by examiner

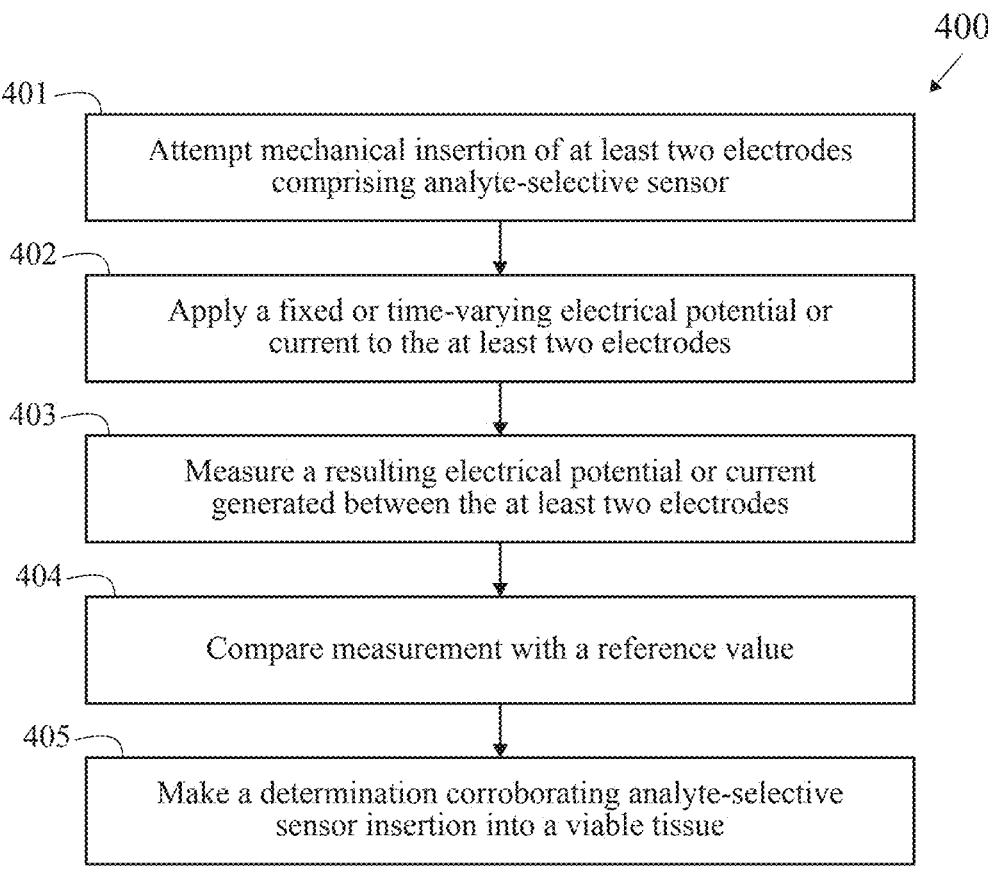

400

401 — Attempt mechanical insertion of at least two electrodes comprising analyte-selective sensor 402 — Apply a fixed or time-varying electrical potential or current to the at least two electrodes 403 — Measure a resulting electrical potential or current generated between the at least two electrodes 404 — Compare measurement with a reference value 405 — Make a determination corroborating analyte-selective sensor insertion into a viable tissue

FIG. 4

METHOD AND SYSTEM FOR CONFIRMATION OF MICRONEEDLE-BASED ANALYTE-SELECTIVE SENSOR INSERTION INTO VIABLE TISSUE VIA ELECTRICAL INTERROGATION

CROSS REFERENCE TO RELATED APPLICATION

The Present Application claims priority to U.S. Patent Application No. 62/542,774, filed on Aug. 8, 2017, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to micro-needle sensors.

Description of the Related Art

The ability to confirm the insertion of a microneedle-based analyte-selective sensor into viable tissue is of paramount importance in the electrochemical sensors domain. Although corroborating insertion of needle-based sensors is quite straightforward owing to the intrinsic macro-scale geometry of such devices and extent of penetration into tissue, as sensors are further miniaturized and penetration into viable tissues becomes more superficial, the assessment of proper insertion grows in importance. Often, when attempts are made to insert micron-scale analyte-selective sensors, such as microneedles, into viable tissues, this typically involves assessing if the absolute levels of signal generated by said sensors reside in a reasonable and expected range of values. Indeed, the ability to corroborate appropriate sensor insertion and persistence in viable tissue has posed a formidable challenge to those aiming to create intracutaneously- and subcutaneously-implanted micron-scale electrochemical sensors for the quantification of circulating analytes in physiological fluids.

In order to ensure proper operation of a microneedle-based analyte-selective sensor in vivo, successful insertion of said sensor must be corroborated, otherwise accurate readings may be compromised.

Prior art solutions have been concerned with visual inspection of analyte-selective sensor insertion—successful insertion of a macro-scale sensor is straightforward to observe. Such a technique, however, is not amenable as the size of said sensor scales to microscopic levels, as is the case with microneedle sensors, whose dimensions fall within 20-2000 μm. Under such circumstances, normal operation is instigated and it is often left to the user to determine if the ensuing measurement resides within an expected range.

Prior art solutions have also been concerned with the user's perception of pain or discomfort upon analyte-selective sensor insertion owing to the permeation of the nerve layer in the dermis, hypodermis, and muscle tissues. As these sensors are further miniaturized and insertion becomes increasingly superficial, the permeation of the nerve layer might be avoided entirely. Hence, even upon proper insertion, a pain or discomfort sensation might not be readily apparent.

Such prior art includes the following.

Brister et al., U.S. Pat. No. 7,905,833 for a Transcutaneous analyte sensor discloses systems and methods for measuring an analyte in a host. More particularly, the Brister relates to systems and methods for transcutaneous measurement of glucose in a host.

Hayter et al., U.S. Pat. No. 9,008,743 for a Method and apparatus for providing data processing and control in medical communication system, discloses methods and apparatus for providing data processing and control for use in a medical communication system are provided.

Angel et al., U.S. Pat. No. 7,645,263 for an Impedance Sensor, discloses a transdermal transport device includes a reservoir for holding a formulation of an active pharmaceutical ingredient, a needle with a bore through which the formulation is transported between the reservoir and a target area of a biological body, and an impedance sensor. The impedance sensor has an electrode positioned to measure the impedance of a portion of the target area between the needle and the electrode to indicate the depth of penetration of the needle into the target area.

Liang et al., U.S. Pat. No. 8,160,834 for Methods and systems for observing sensor parameters, discloses methods and materials for observing the state of a sensor, for example those used by diabetic patients to monitor blood glucose levels. Typically a voltage such as a voltage pulse is applied to the sensor in order to solicit a current response from which for example, factors such as impedance values can be derived. Such values can then be used as indicators of a sensor's state, for example the state of sensor hydration, sensor noise, sensor offset, sensor drift or the like.

BRIEF SUMMARY OF THE INVENTION

The technology described herein relates to implantable, analyte-selective microneedle sensors and operation of the same.

The current invention teaches of a method for the identification of successful insertion of a microneedle-based analyte-selective sensor into a viable tissue, including the epidermis, dermis, and hypodermis. Mechanical insertion of an analyte-selective sensor is firstly attempted by means of an application of external force. Either during or following this routine, an electrical stimulus is applied between at least two distinct electrodes located within the said analyte-selective sensor; a resultant response is measured. This response is compared with a reference value to determine if insertion was successful. If insertion was successful, no further effort is required and the sensor can operate as intended. However, if insertion was not successful, the user can be instructed to continue to apply additional force to said sensor to achieve successful insertion or otherwise re-apply the said sensor altogether.

One aspect of the present invention is a method to confirm the insertion of an analyte-selective sensor comprising an array of microneedles possessing vertical extent between 200 and 2000 μm into viable tissue. The method includes attempting mechanical insertion of at least two spatially-distinct microneedle structures on said array, each featuring a single electrode, into a viable tissue. The method also includes applying a fixed or time-varying electrical potential or current to the at least two electrodes following said attempt at mechanical insertion. The method also includes measuring the resultant electrical potential, current, resistance, conductance, capacitance, or impedance value generated between the two electrodes and comparing said value to a known reference value to corroborate successful insertion and in situ access to said viable tissue.

Another aspect of the present invention is a method to confirm the insertion of a microneedle-based analyte-selective sensor into cutaneous tissue. The method includes attempting mechanical insertion of at least two electrodes comprising said analyte-selective sensor into the cutaneous tissue. The method also includes applying a fixed or time-varying electrical potential or current to the at least two electrodes following said attempt at mechanical insertion. The method also includes measuring the resultant electrical potential, current value generated between said two electrodes and comparing said value to a known reference value to corroborate successful insertion and in situ access to said cutaneous tissue.

Yet another aspect of the present invention is a method to activate a microneedle-based analyte-selective sensor by completing an electrical circuit upon the successful mechanical insertion of at least two spatially-distinct microneedle structures on said sensor, each microneedle constituent featuring a single electrode, into a viable tissue, thereby transitioning said sensor from an OFF/hibernate to ON/active state.

Yet another aspect of the present invention is a method to confirm the insertion of a microneedle-based analyte-selective sensor into cutaneous tissue. The method includes inserting into cutaneous tissue of a user at least two spatially-distinct microneedle structures of an array, each spatially-distinct microneedle structure comprising a single electrode and extending between 200 and 2000 μm from a base of the array. The method also includes applying a fixed or time-varying electrical potential or current to the at least two electrodes following the insertion into the cutaneous tissue. The method also includes measuring a resultant electrical potential, current value generated between the at least two electrodes. The method also includes comparing the value to a known reference value to corroborate successful insertion and in situ access to the cutaneous tissue of the user.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 4 is a block/process flow diagram illustrating the process flow to corroborate successful sensor insertion.

DETAILED DESCRIPTION OF THE INVENTION

Figure 1:
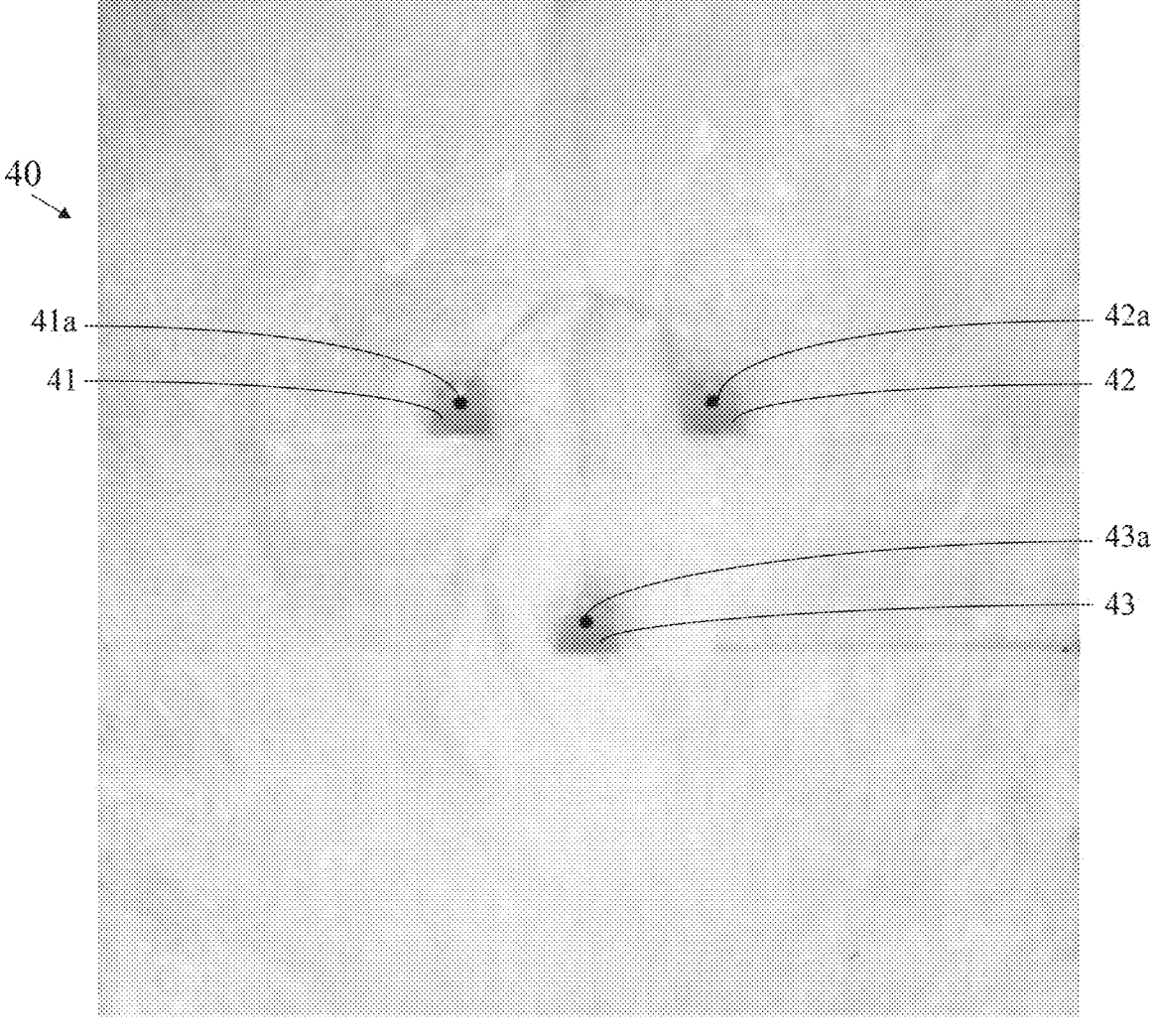
FIG. 1 illustrates an analyte-selective sensor featuring three microneedle structures, each measuring 1200 μm in vertical extent and designed to permeate the stratum corneum to access the interstitial fluid occupying the viable dermis.

The current invention represents a simple and straight-forward approach facilitating the confirmation of a successful sensor insertion event; the disclosed technique addresses the shortcomings of the prior art while remaining amenable to established methods of applying intracutaneous and intradermal analyte-selective electrochemical sensors.

In order to tender accurate physiological or physiochemical readings of a particular analyte or group of analytes, an analyte-selective electrochemical sensor must remain in fluidic contact with the tissue, physiological fluid, or physiological compartment of interest and, often, the active sensing region of said electrochemical sensor must maintain full immersion or coverage within the said tissue, physiological fluid, or physiological compartment. This has not posed a noteworthy challenge in the past as analyte-selective sensors have exhibited sufficiently large geometries to ensure that improper sensor insertion can be seen by the naked eye. As sensors have increasingly miniaturized over the years, such as the case with the emergence of microneedle-based analyte-selective sensors, this method has not sufficed. Accordingly, the only viable method capable of addressing this challenge is via electrical interrogation of the said sensor to corroborate successful insertion or to confirm that said sensor remains inserted. Under these embodiments, the user must decide if the reading tendered by the sensor lies within a reasonable or otherwise expected value or range of values. In certain scenarios, a priori knowledge of the reading might be impossible or, at the least, difficult to ascertain.

The technology disclosed herein teaches of a method to circumvent the challenge of assessing if a microneedle-based analyte-selective electrochemical sensor has penetrated/permeated a biological interface and accessed a viable tissue, physiological fluid, or physiological compartment. Specifically, mechanical insertion of at least two spatially distinct electrodes comprising said microneedle-based analyte-selective sensor is attempted in order to penetrate/permeate a biological interface; this is realized by the application of an external physical force by hand or by an external mechanical apparatus.

For the sake of clarity, each microneedle structure features a unique and addressable electrode element and each analyte-selective sensor contained at least two microneedle structures, possessing vertical extent between 20 and 2000 μm, disposed therein. During or after said insertion process, an excitation circuit, embedded in the analyte-selective sensor, applies a fixed or time-varying electrical potential or current to the at least two electrodes located on the at least two microneedle structures. Said fixed or time-varying electrical potential or current interacts at the electrode interface with a tissue, physiological fluid, physiological compartment, or lack thereof, and is thereby modulated in amplitude, frequency, and/or phase, reflecting a change in at least one of a resistance, conductance, capacitance, inductance, or impedance. A measurement circuit subsequently transduces said modulated electrical potential or current generated between the at least two electrodes to the digital domain by means of analog-to-digital conversion.

The quantized, digital value of said modulated electrical potential or current is compared with a pre-programmed threshold or range and a decision circuit determines if the quantized, digital value lies above or below said pre-programmed threshold or within or beyond said pre-programmed range. A YES/NO assessment of sensor insertion into a viable tissue, physiological fluid, or physiological compartment is thus made based on this comparison. Optionally, the analyte-selective sensor system can inform the user via audible, visual, or haptic feedback that said analyte-selective sensor has been satisfactorily inserted and, if not, the system can alternatively direct the user to apply additional external physical force by hand or by an external mechanical apparatus to achieve satisfactory insertion based on the above assessment process. Otherwise, the user can be instructed to remove and re-apply said sensor. In this fashion, a system-directed indication is tendered to the user that provides definitive confirmation of penetration/permeation of a biological interface or membrane and access to a tissue, physiological fluid, or physiological compartment without requiring visual observation of insertion or a user-based assessment of the validity of said analyte-selective sensor readings.

Alternatively, during said insertion process, an excitation circuit, embedded in the analyte-selective sensor, applies an electrical potential, which can also comprise a ground or '0' potential, to the at least two electrodes located on the at least two microneedle structures. When said insertion process is not successful and the electrode interface fails to access said tissue, physiological fluid, or physiological compartment, the excitation circuit is not completed and no (or a negligible amount of) current can flow between said at least two electrodes. Under this scenario, the device cannot activate or power to an 'ON' state. Alternatively, upon suitable insertion of said at least two electrodes located on the at least two microneedle structures into tissue, physiological fluid, or physiological compartment, owing to the high conductivity of said tissue, physiological fluid, or physiological compartment, the said excitation circuit is completed and a current may flow, thereby causing the device to active or power to an 'ON' state.

FIG. 1 illustrates an analyte-selective sensor 40 featuring three microneedle structures 41, 42 and 43, each measuring 1200 μm in vertical extent and designed to permeate the stratum corneum to access the interstitial fluid occupying the viable dermis. Each microneedle structure 41, 42, and 43 contains an individually-addressable metal electrode disposed in the circular aperture 41a, 42a and 43a located therein.

Figures 2, 2A:
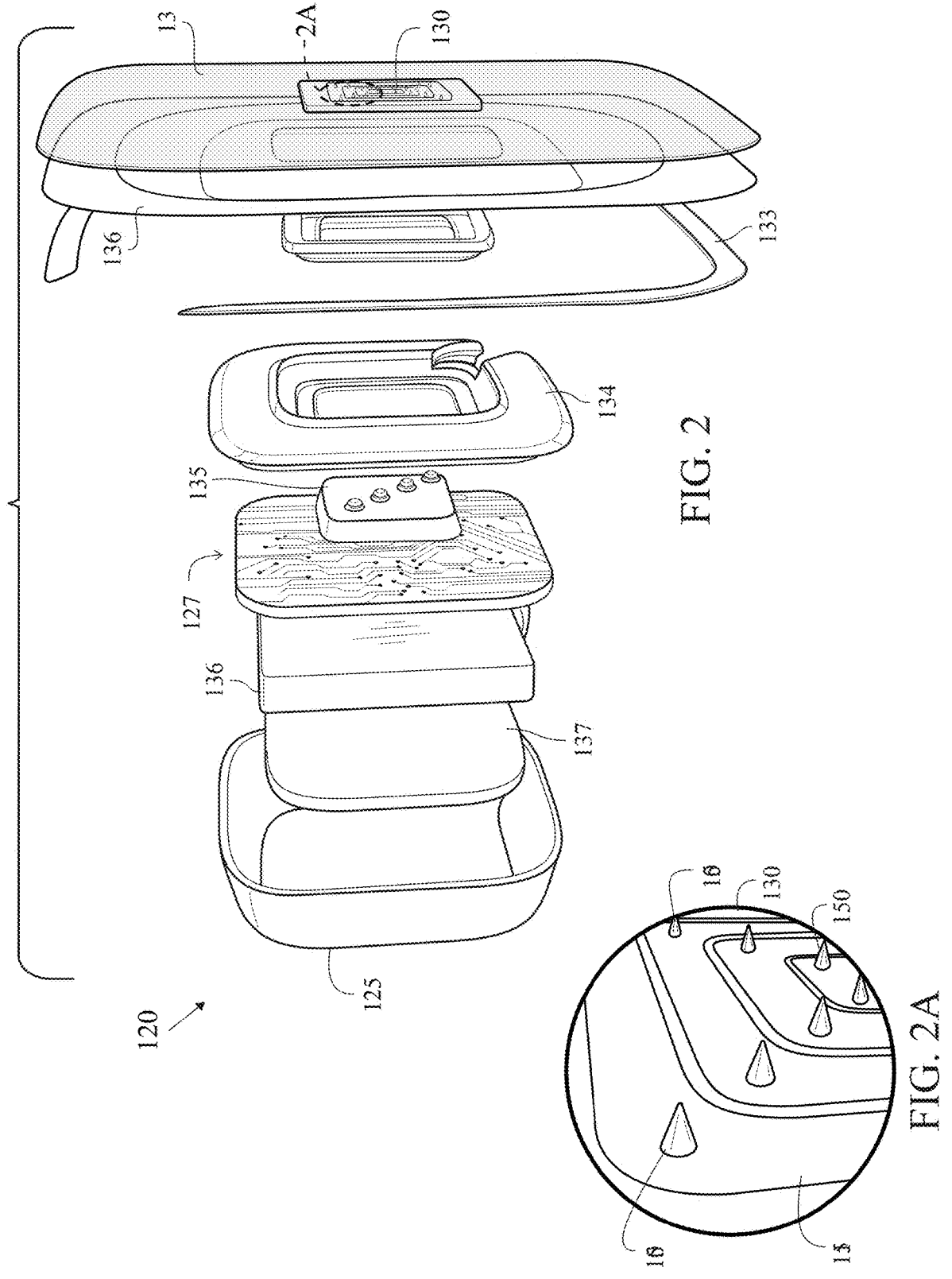
FIG. 2 is an exploded view of a microneedle-based analyte-selective sensor system with the microneedle array and excitation and measurement circuit shown.
FIG. 2A is an expanded view of the microneedle constituents is provided in circle 2A of FIG. 2.

FIG. 2 is an exploded view of a microneedle-based analyte-selective sensor system with the microneedle array 120 and excitation and measurement circuit shown. An expanded view of the microneedle constituents is provided in FIG. 2A. The microneedle biosensing sensor 120 preferably comprises a housing member 125, a back plate 137, an internal pad 136, a circuit board cover 1314, an external pad 133, and adhesive pad, a front panel 131 a microneedle biosensor 130 with microneedles 150, and a printed circuit board 127 containing the electronic circuitry required to transduce biochemical signals to digital data that are wirelessly transmitted to an external device via the embedded wireless transceiver. An electrochemical analog front end preferably includes: a Texas Instruments LMP91000 Sensor AFE System, configurable AFE potentiostat for low-power chemical sensing applications; a Texas Instruments LMP91200 configurable AFE for low-power chemical sensing applications; or an Analog Devices ADuCM350 16-Bit Precision, low power meter on a chip with Cortex-M3 and connectivity. The wireless transceiver is preferably is a BLUEGIGA BLE-113A BLUETOOTH Smart Module, or a Texas Instruments CC2540 SimpleLink BLUETOOTH Smart Wireless MCU with USB.

Figure 3:
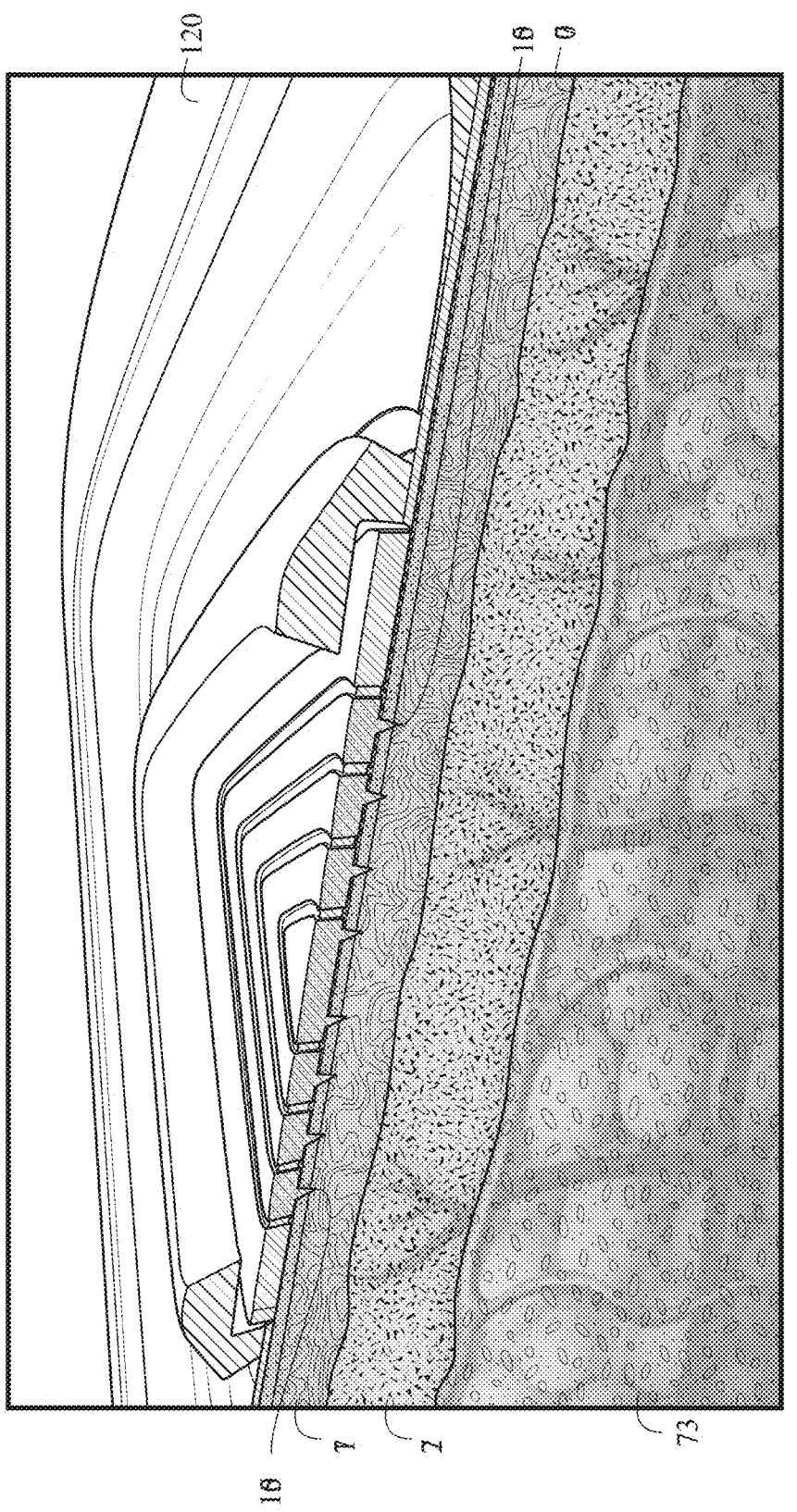
FIG. 3 is a cutaway view of a microneedle-based analyte-selective sensor system illustrating successful permeation/penetration of the stratum corneum (brown) to access the viable dermis (pink).

FIG. 3 is a cutaway view of a microneedle-based analyte-selective sensor system 120 with micro-needles 150 successfully penetrating the stratum corneum 70 to access the viable dermis 71.

FIG. 4 is a block/process flow diagram illustrating a method 400 to confirm the insertion of a microneedle-based analyte-selective sensor into viable tissue. At block 401, at least two spatially-distinct microneedle structures of an array are inserted into cutaneous tissue of a user. The tissue includes an organ, a membrane, a physiological compartment, and a physiological fluid. The insertion is achieved by means of application of pressure, force velocity or energy to achieve puncture or permeation of the stratum corneum. Each spatially-distinct microneedle structure preferably comprises a single electrode and extends between 200 and 2000 μm from a base of the array. The electrodes comprise metal, semiconductor, or organic surfaces of defined geometry. At block 402, a fixed or time-varying electrical potential or current is applied to the at least two electrodes following the insertion into the cutaneous tissue. The fixed or time-varying electrical potential or current includes a constant voltage, voltage waveform, direct current, alternating current, sinusoidal signal, frequency-dependent signal, impulse, a constant phase signal, and a varying-phase signal. The electrical potential is preferably between zero and one Volt. The electrical current is preferably between one femto-ampere and ten milli-amperes. At block 403, a resultant electrical potential, current value generated between the at least two electrodes is measured. At block 404, the current value is compared to a known reference value to corroborate successful insertion and in situ access to the cutaneous tissue of the user. The reference value includes a voltage, a current, a resistance, a conductance, a capacitance, an inductance, and an impedance. The reference value is set between the preferred electrical potential (one to one Volt) or the preferred electrical current (one femto-ampere and ten milli-amperes). At block 405, a determination is made that the microneedle-based analyte-selective sensor has been successfully inserted into cutaneous tissue.

FIGS. 5, 5A, 5B and 5C are a diagrammatic representation of a decision tree delineating the assessment of tissue penetration and hence sensor insertion. The decision tree operates in an embedded system paired to a tissue-penetrating analyte-selective sensor. FIGS. 5, 5A, 5B and 5C illustrate several different electrical methods used to interrogate the electrodes to determine successful insertion into tissue.

Figure 5:
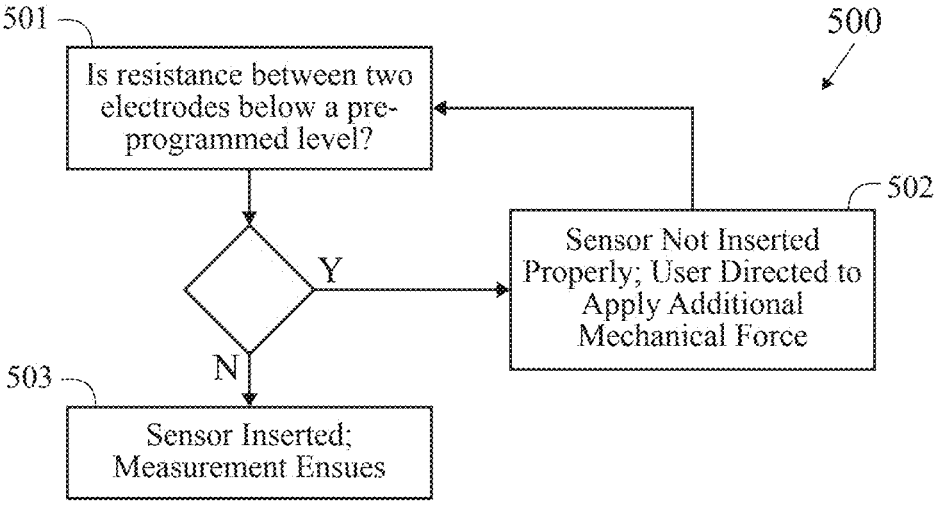
FIG. 5 is a diagrammatic representation of a decision tree delineating the assessment of tissue penetration and hence sensor insertion.

As shown in FIG. 5, decision tree 500 begins at block 501 inquiring if a resistance between two electrodes is below a pre-programmed level. If yes, at block 502 the sensor is not inserted properly and the user is directed to apply additional mechanical force. If no, at block 503 the sensor is inserted properly and the measurement is conducted.

Figure 5A:
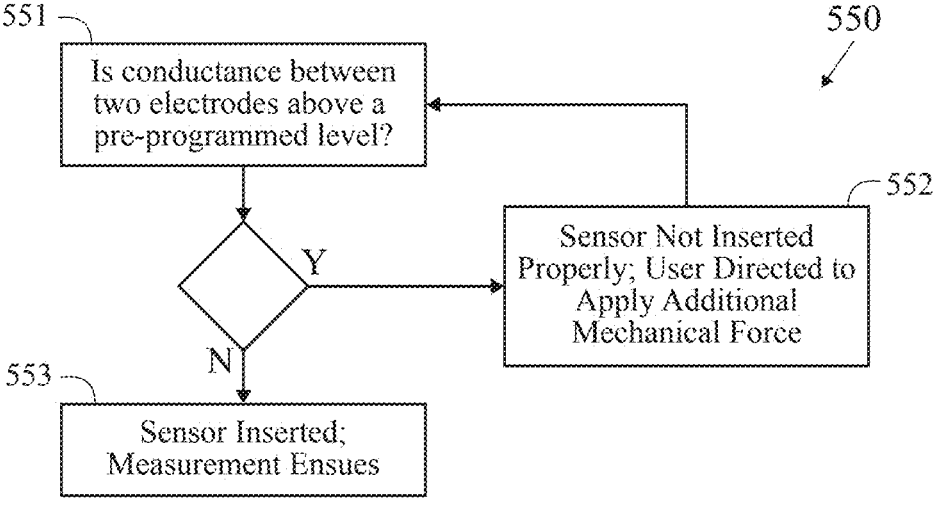
FIG. 5A is a diagrammatic representation of a decision tree delineating the assessment of tissue penetration and hence sensor insertion.

As shown in FIG. 5A, decision tree 550 begins at block 551 inquiring if a conductance between two electrodes is above a pre-programmed level. If yes, at block 552 the sensor is not inserted properly and the user is directed to apply additional mechanical force. If no, at block 553 the sensor is inserted properly and the measurement is conducted.

Figure 5B:
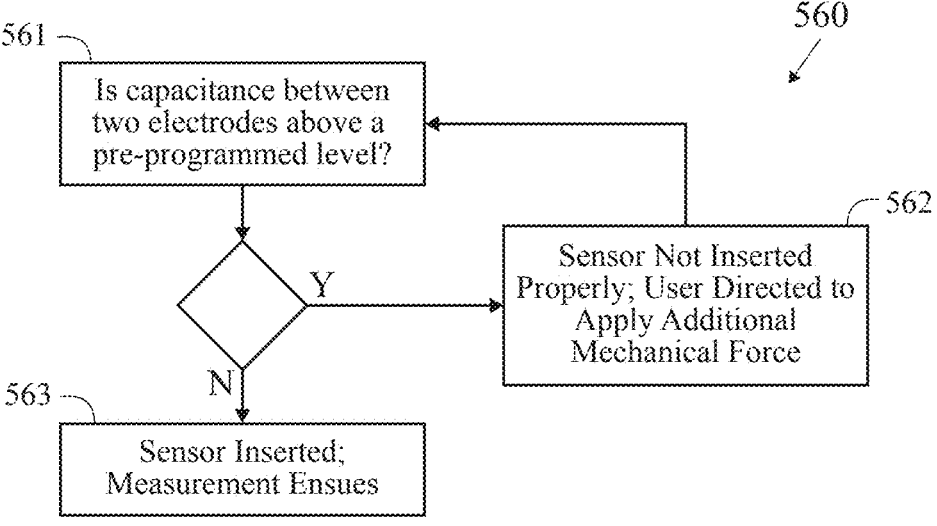
FIG. 5B is a diagrammatic representation of a decision tree delineating the assessment of tissue penetration and hence sensor insertion.

As shown in FIG. 5B, decision tree 560 begins at block 561 inquiring if a capacitance between two electrodes is above a pre-programmed level. If yes, at block 562 the sensor is not inserted properly and the user is directed to apply additional mechanical force. If no, at block 563 the sensor is inserted properly and the measurement is conducted.

Figure 5C:
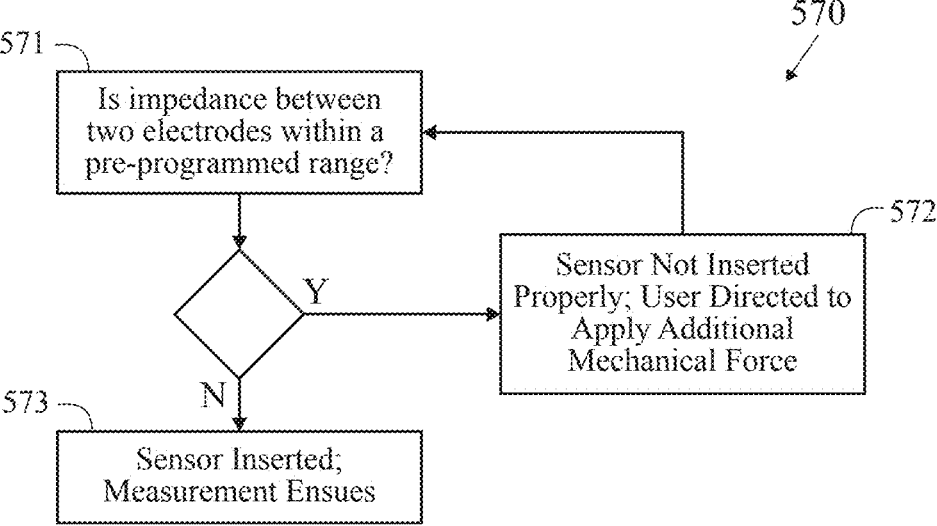
FIG. 5C is a diagrammatic representation of a decision tree delineating the assessment of tissue penetration and hence sensor insertion.

As shown in FIG. 5C, decision tree 570 begins at block 551 inquiring if an impedance between two electrodes is within a pre-programmed range. If yes, at block 572 the sensor is not inserted properly and the user is directed to apply additional mechanical force. If no, at block 573 the sensor is inserted properly and the measurement is conducted.

Figure 6:
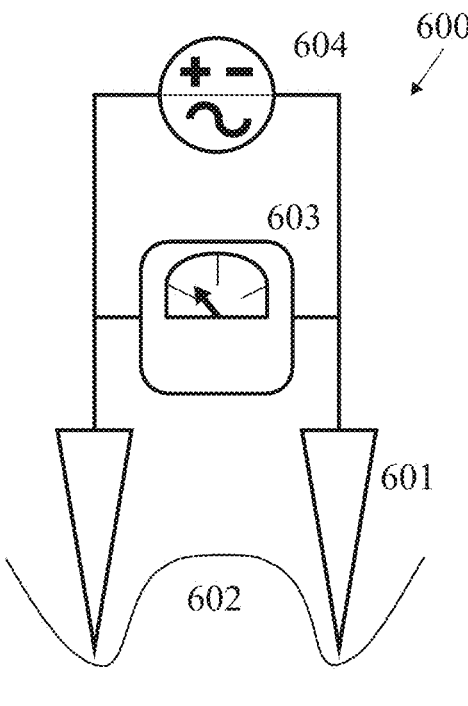
FIG. 6 is a diagrammatic representation of analyte-selective sensor featuring electrodes that have not successfully penetrated/permeated a biological interface/tissue, as determined by a measurement circuit.
Figure 6A:
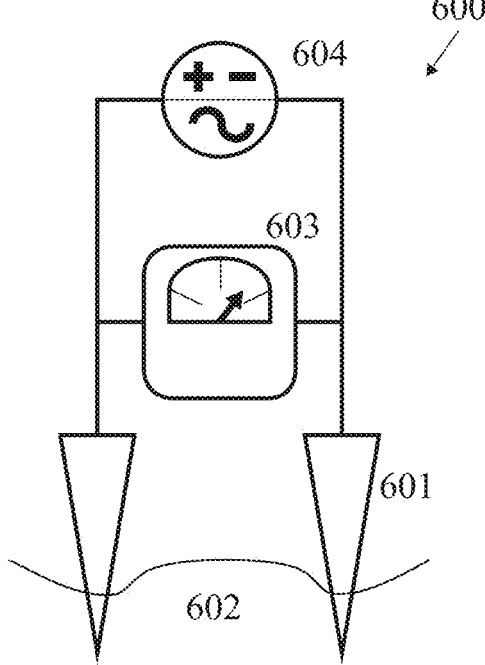
FIG. 6A is a diagrammatic representation of analyte-selective sensor featuring electrodes that have successfully penetrated/permeated a biological interface/tissue, as determined by a measurement circuit.

FIG. 6 is a diagrammatic representation of analyte-selective sensor 600 featuring electrodes 601 that have not successfully penetrated/permeated a biological interface/tissue 602, as determined by a measurement circuit 603. The excitation circuit 604 provides the probe signal required to interrogate the electrodes. FIG. 6A is a diagrammatic representation of analyte-selective sensor 600 featuring electrodes 601 that have successfully penetrated/permeated a biological interface/tissue 602, as determined by a measurement circuit 603. The excitation circuit 604 provides the probe signal required to interrogate the electrodes. For the sake of clarity, elements 601, 602 and 603 comprise key constituents of the analyte-selective sensor.

A microneedle-based analyte-selective sensor is a measurement system, containing the below elements, that enables the quantification or assessment of absolute or relative levels of a biological analyte located within a tissue, physiological fluid, or physiological compartment.

Two (or more) electrodes (contained within analyte-selective sensor and designed to reside in the sensing medium) which serving as an electrical-to-biological transducer, provides a means to interface an electronic circuitry with a biological tissue. At least two electrodes are required to form a complete electrical circuit.

An excitation circuit (contained within analyte-selective sensor) provides an electrical excitation signal, stimulus, or probe to interrogate said electrodes.

A measurement circuit (contained within analyte-selective sensor) measures an electrical response generated at the electrode surface in response to said excitation signal, stimulus, or probe.

An embedded decision system makes a determination of sensor penetration/insertion into a viable tissue based on a pre-programmed value, level, or range. Assessment is based on a YES/NO criterion.

McCanna et al., U.S. Pat. No. 9,933,387, for a Miniaturized Sub-Nanoampere Sensitivity Low-Noise Potentiostat System is hereby incorporated by reference in its entirety.

Windmiller et al., U.S. patent application Ser. No. 14/955,850, filed on Dec. 1, 2015, for a Method And Apparatus For Determining Body Fluid Loss is hereby incorporated by reference in its entirety.

Windmiller, U.S. patent application Ser. No. 15/177,289, filed on Jun. 8, 2016, for a Methods And Apparatus For Interfacing A Microneedle-Based Electrochemical Biosensor With An External Wireless Readout Device is hereby incorporated by reference in its entirety.

Wang et al., U.S. Patent Publication Number 20140336487 for a Microneedle Arrays For Biosensing And Drug Delivery is hereby incorporated by reference in its entirety.

Windmiller, U.S. patent application Ser. No. 15/590,105 for a Tissue-Penetrating Electrochemical Sensor Featuring A Co Electrodeposited Thin Film Comprised Of A Polymer And Bio-Recognition Element is hereby incorporated by reference in its entirety.

PCT Publication WO2018/071265 for an Electro-Deposited Conducting Polymers For The Realization Of Solid-State Reference Electrodes For Use In Intracutaneous And Subcutaneous Analyte-selective Sensors is hereby incorporated by reference in its entirety.

Windmiller, U.S. patent application Ser. No. 15/913,709, filed on Mar. 6, 2018 for Methods For Achieving An Isolated Electrical Interface Between An Anterior Surface Of A Microneedle Structure And A Posterior Surface Of A Support Structure is hereby incorporated by reference in its entirety.

Windmiller, U.S. patent application Ser. No. 15/961,793, filed on Apr. 24, 2018 for Heterogeneous Integration of Silicon-fabricated Solid Microneedle Sensors and CMOS Circuitry is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A method to confirm insertion, into cutaneous tissue, of an analyte-selective sensor comprising a first microneedle with a first electrode and a second microneedle with a second electrode, said method comprising:

applying, by an excitation circuit of the analyte-selective sensor and after an attempted insertion of the first and second microneedles into the cutaneous tissue, a first electrical potential to the first and second electrodes;

measuring, by a measurement circuit of the analyte-selective sensor, a resultant electrical value generated between the first and second electrodes through the cutaneous tissue;

comparing the resultant electrical value to a range of values indicative of insertion of the first and second microneedles into the cutaneous tissue; and applying, by the excitation circuit of the analyte-selective sensor and responsive to the comparison indicating insertion of the first and second microneedles into the cutaneous tissue, a second electrical potential to the first and second electrodes, wherein the second electrical potential is greater than the first electrical potential and is used to measure an analyte concentration within physiological fluid.

2. The method of claim 1, wherein said analyte-selective sensor comprises an electrochemical sensor.

3. The method of claim 1, wherein the attempted insertion is achieved by application of pressure, force velocity, or energy, to achieve a penetration of an outer surface of the cutaneous tissue.

4. The method of claim 1, wherein each of the first and second electrodes comprises one or more of a metal, a semiconductor, and an organic surface of a defined geometry.

5. The method of claim 1, wherein the first electrical potential is a fixed or time-varying electrical potential comprising a constant voltage, a voltage waveform, a sinusoidal signal, a frequency-dependent signal, an impulse, a constant phase signal, or a varying-phase signal.

6. The method of claim 1, wherein the range of values comprises a range of voltage, current, resistance, conductance, capacitance, inductance, or impedance values.

7. A method to confirm insertion, into cutaneous tissue, of a microneedle-based analyte-selective sensor, said method comprising:

applying, by an excitation circuit of the analyte-selective sensor and after an attempted insertion into the cutaneous tissue of at least two electrodes of the analyte-selective sensor, a first electrical potential to the at least two electrodes;

measuring, by a measurement circuit of the analyte-selective sensor, a resultant electrical value generated between the at least two electrodes through the cutaneous tissue;

comparing the resultant electrical value to a range of values indicative of insertion of the at least two electrodes into the cutaneous tissue; and applying, by the excitation circuit of the analyte-selective sensor and responsive to the comparison indicating insertion of the at least two electrodes of analyte-selective sensor into the cutaneous tissue, a second electrical potential to the at least two electrodes, wherein the second electrical potential is greater than the first electrical potential and is used to measure an analyte concentration within physiological fluid.

8. The method of claim 7, wherein said cutaneous tissue comprises the epidermis, dermis, or hypodermis.

9. The method of claim 7, wherein the attempted insertion is achieved by application of pressure, force velocity, or energy, to achieve a penetration of an outer surface of the cutaneous tissue.

10. The method of claim 7, wherein each of said at least two electrodes comprises one or more of a metal, a semiconductor, and an organic surface of a defined geometry.

11. The method of claim 7, wherein the first electrical potential is a fixed or time-varying electrical potential comprising a constant voltage, a voltage waveform, a sinusoidal signal, a frequency-dependent signal, an impulse, a constant phase signal, or a varying-phase signal.

12. The method of claim 7, wherein the range of values comprises a range of voltage, current, resistance, conductance, capacitance, inductance, or impedance values.

13. A method to confirm insertion, into cutaneous tissue, of an analyte-selective sensor comprising a microneedle array, said method comprising:

applying, by an excitation circuit of the analyte-selective sensor, a first electrical potential to at least two electrodes of the microneedle array following an attempted insertion of the microneedle array into the cutaneous tissue;

measuring, by a measurement circuit of the analyte-selective sensor, a resultant electrical value generated between the at least two electrodes through the cutaneous tissue;

comparing the resultant electrical value to a range of values indicative of insertion into the cutaneous tissue; and applying, by the excitation circuit of the analyte-selective sensor and responsive to the comparison indicating insertion of the microneedle array into the cutaneous tissue, a second electrical potential to the at least two electrodes, wherein the second electrical potential is greater than the first electrical potential and is used to measure an analyte concentration within physiological fluid.

14. The method according to claim 13, wherein the attempted insertion is achieved by application of pressure, force velocity, or energy, to achieve a penetration of an outer surface of the cutaneous tissue.

15. The method according to claim 13, wherein the first electrical potential is a fixed or time-varying electrical potential comprising one of a constant voltage, a voltage waveform, a sinusoidal signal, a frequency-dependent signal, an impulse, a constant phase signal, or a varying-phase signal.

16. The method according to claim 13, wherein the range of values comprises a range of voltage, current, resistance, conductance, capacitance, inductance, or impedance values.

17. A method of an analyte-selective sensor comprising a first microneedle with a first electrode and a second microneedle with a second electrode, said method comprising:

applying, by an excitation circuit of the analyte-selective sensor and after an attempted insertion of the first and second microneedles into cutaneous tissue of a user, a first electrical potential to the first and second electrodes;

measuring, by a measurement circuit of the analyte-selective sensor, a first resultant electrical value generated between the first and second electrodes through the cutaneous tissue;

comparing the resultant electrical value to a range of values indicative of insertion of the first and second microneedles into the cutaneous tissue;

providing, when the comparison indicates insertion of the first and second microneedles into the cutaneous tissue is not achieved, a direction to the user to apply a force to the analyte-selective sensor to attempt re-insertion of the analyte-selective sensor;

applying, by the excitation circuit of the analyte-selective sensor and after the attempted re-insertion of the first and second microneedles into the cutaneous tissue of the user, a second electrical potential to the first and second electrodes;

measuring, by the measurement circuit of the analyte-selective sensor, a second resultant electrical value generated between the first and second electrodes through the cutaneous tissue;

comparing the resultant electrical value to the range of values indicative of insertion of the first and second microneedles into the cutaneous tissue; and applying, by the excitation circuit of the analyte-selective sensor and when the comparison indicates insertion of the first and second microneedles into the cutaneous tissue, a third electrical potential to the first and second electrodes, wherein the third electrical potential is greater than the first electrical potential and the second electrical potential.

18. The method of claim 17, wherein the application of the force in response to the direction is applied by a hand of the user.

* * * * *